United States Patent
Je et al.

(10) Patent No.: US 9,324,504 B2
(45) Date of Patent: Apr. 26, 2016

(54) ORGANIC METAL DYE, AND PHOTOELECTRIC ELEMENT AND DYE-SENSITIZED SOLAR CELL USING THE ORGANIC METAL DYE

(75) Inventors: Jongtae Je, Cheongju-si (KR); Sungouk Jung, Cheongju-si (KR); Sanghae Lee, Daejeon (KR); Jeageon Lim, Cheongju-si (KR)

(73) Assignee: SFC CO., LTD. (KR)

( * ) Notice: Subject to any disclaimer, the term of this patent is extended or adjusted under 35 U.S.C. 154(b) by 816 days.

(21) Appl. No.: 13/513,103

(22) PCT Filed: Dec. 1, 2010

(86) PCT No.: PCT/KR2010/008515
§ 371 (c)(1),
(2), (4) Date: May 31, 2012

(87) PCT Pub. No.: WO2011/068346
PCT Pub. Date: Jun. 9, 2011

(65) Prior Publication Data
US 2012/0247546 A1  Oct. 4, 2012

(30) Foreign Application Priority Data
Dec. 2, 2009  (KR) .................. 10-2009-0118654

(51) Int. Cl.
| | | |
|---|---|---|
| *C07F 15/00* | (2006.01) |
| *H01L 51/46* | (2006.01) |
| *H01L 51/44* | (2006.01) |
| *H01G 9/20* | (2006.01) |
| *C09B 57/10* | (2006.01) |
| *H01L 51/00* | (2006.01) |

(52) U.S. Cl.
CPC .......... *H01G 9/2059* (2013.01); *C07F 15/0053* (2013.01); *C09B 57/10* (2013.01); *H01L 51/0086* (2013.01); *H01G 9/2031* (2013.01); *Y02E 10/52* (2013.01); *Y02E 10/542* (2013.01); *Y02E 10/549* (2013.01)

(58) Field of Classification Search
CPC .... H01G 9/2059; H01G 9/2031; C09B 57/10; H01L 51/0086; C07F 15/0053; Y02E 10/549; Y02E 10/52
See application file for complete search history.

(56) References Cited

U.S. PATENT DOCUMENTS

| 7,538,217 B1 | 5/2009 | Lin et al. |
| 2008/0169022 A1* | 7/2008 | Matsui et al. .................. 136/256 |

FOREIGN PATENT DOCUMENTS

| KR | 1020070073045 A | 7/2007 |
| KR | 1020070075186 A | 7/2007 |
| KR | 1020080049197 A | 6/2008 |

OTHER PUBLICATIONS

Tan et al., "Nuclear Permeable Ruthenium(II) B-Carboline Complexes Induce Autophagy to Antagonize Mitochondrial—Mediated Apoptosis," J. Med. Chem., 2010, 53, 7613-7624.*
International Search Report (in Korean with English Translation) and Written Opinion (in Korean) for PCT/KR2010/008515, mailed Aug. 12, 2011; ISA/KR.

* cited by examiner

*Primary Examiner* — Ling Choi
*Assistant Examiner* — Catherine S Branch
(74) *Attorney, Agent, or Firm* — Harness, Dickey & Pierce, P.L.C.

(57) ABSTRACT

The present invention relates to an organic metal dye comprising fused heterocyclic derivatives, and to a photoelectric element and to a dye-sensitized solar cell using the organic metal dye.

15 Claims, 3 Drawing Sheets

ORGANIC METAL DYE, AND PHOTOELECTRIC ELEMENT AND DYE-SENSITIZED SOLAR CELL USING THE ORGANIC METAL DYE

TECHNICAL FIELD

The present invention relates to an organic metal dye, and a photoelectric element, and a dye-sensitized solar cell using the same.

BACKGROUND ART

A photoelectric element is an element for converting light energy into electric energy. A representative photoelectric element is a solar cell.

A dye-sensitized solar cell, that is, a kind of solar cell, was representatively reported by Gratzel, et al in Switzerland. A dye used for the dye-sensitized solar cell may be largely divided into an organic metal dye and an organic dye according to the use or non-use of an organic metal.

The organic dye is required to have characteristics such as a high light absorptivity, and a wide absorption wavelength band.

DETAILED DESCRIPTION OF THE INVENTION

Technical Problem

Therefore, a first object of the present invention is to provide an organic metal dye including a fused heterocyclic derivative, which has a high light absorptivity and an absorption band in a long wavelength.

Also, a second object of the present invention is to provide a photoelectric element and a dye-sensitized solar cell, which employ an organic metal dye, and thus has improved properties.

Technical Solution

In accordance with an aspect of the present invention, there is provided an organic metal dye represented by Formula below.

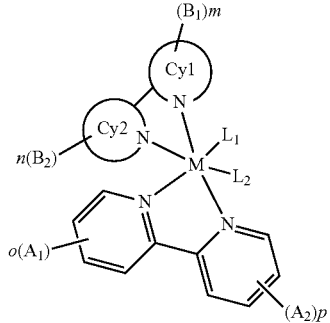

In accordance with another aspect of the present invention, there is provided a photoelectric element and a dye-sensitized solar cell, which include an organic metal dye represented by Formula above.

Advantageous Effects

The present invention provides an organic metal dye having a high light absorptivity and photoelectric conversion efficiency, and a photoelectric element, and a dye-sensitized solar cell using the organic metal dye.

MODE FOR CARRYING OUT THE INVENTION

Figure 1:
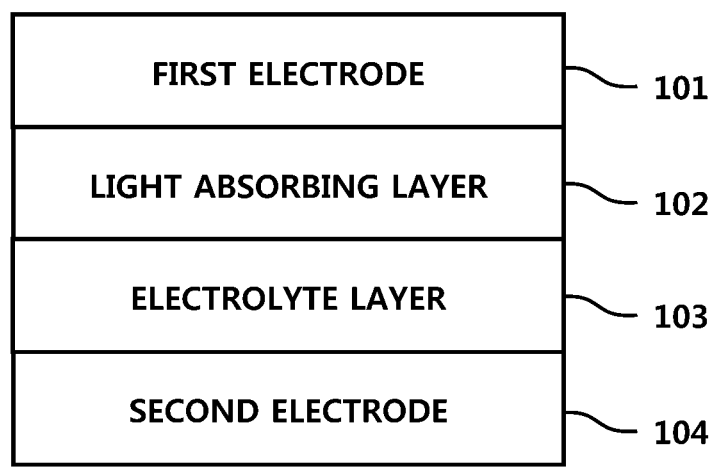
FIG. 1 shows a dye-sensitized solar cell according to an embodiment of the present invention.

Hereinafter, exemplary embodiments of the present invention will be described with reference to the accompanying drawings. In the following description, the same elements will be designated by the same reference numerals although they are shown in different drawings. Further, in the following description of the present invention, a detailed description of known functions and configurations incorporated herein will be omitted when it may make the subject matter of the present invention rather unclear.

Also, in description of components of an embodiment of the present invention, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

The present invention provides an organic metal dye represented by Formula 1 below.

[Formula 1]

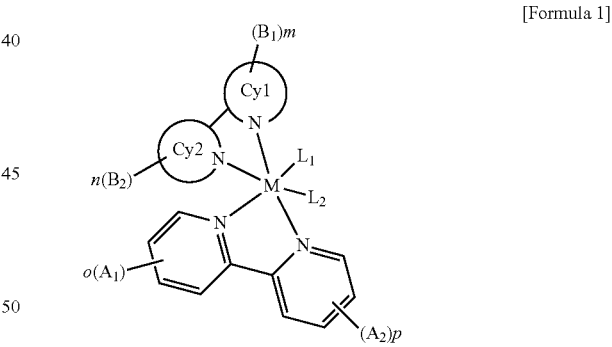

In Formula 1, Cy1, and Cy2 each may represent a pyridine group or a nitrogen-containing fused heteroaryl group having 5 to 40 carbon atoms, M may represent a metal selected from the group including Ru, Os and Fe, and $L_1$ and $L_2$ each may be independently selected from the group including $H_2O$, —Cl, —I, —CN, —NCO and —NCSe.

$A_1, A_2, B_1$ and $B_2$ each may be independently selected from the group including substituted or unsubstituted alkyl, substituted or unsubstituted alkenyl, substituted or unsubstituted alkynyl, substituted or unsubstituted aryl and substituted or unsubstituted heteroaryl, and may include continuous bonds of several functional groups. Herein, at least one of $A_1, A_2, B_1$ and $B_2$ may include at least one anchoring group selected from the group including COOH, $PO_3H_2$, $PO_4H_2$, $SO_4H_2$, CONHOH or a deprotonated form thereof. As the deprotonated form, one or more terminal groups of a dye may form an anion, and may form a salt in combination with a cation. The cation may be selected from the group including ammonium, phosphonium, sulfonium, imidazolium, pyrrolidonium and pyridinium although it is not particularly limited thereto.

m, n, o and p each may be an integer from 1 to 20. When m to p each is an integer greater than 1, a plurality of $A_1$, $A_2$, $B_1$ and $B_2$ may be independently same or different.

In Formula 1, a substituent used in $Cy_1$, $Cy_2$, $A_1$, $A_2$, $B_1$ and $B_2$ may be selected from the group including a hydrogen atom, a deuterium atom, a halogen atom, a cyano group, a nitro group, a C1 to C10 alkyl silyl group, a C1 to C40 alkyl group, a C1 to C40 alkoxy group, a C1 to C40 alkyl amino group, a C6 to C40 aryl group, a C6 to C40 aryloxy group, a C6 to C40 arylamino group, a C6 to C40 arylsilyl group, and a C3 to C40 heteroaryl group.

$Cy_1$, $Cy_2$, $A_1$, $A_2$, $B_1$, $B_2$, and the substituent may be linked to each other to form a saturated or unsaturated ring.

Also, the present invention may provide an organic metal dye represented by Formula 2 below.

[Formula 2]

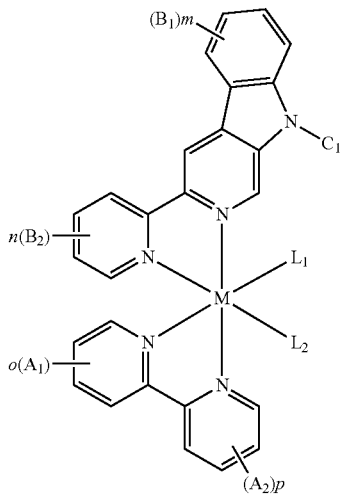

In Formula 2, $A_1$, $A_2$, $B_1$, $B_2$, M, $L_1$, $L_2$, m, n, o and p may be the same as those in Formula 1 above, and $C_1$ may be the same as $B_1$ in Formula 1.

Also, the present invention may provide an organic metal dye represented by Formula 3 below.

[Formula 3]

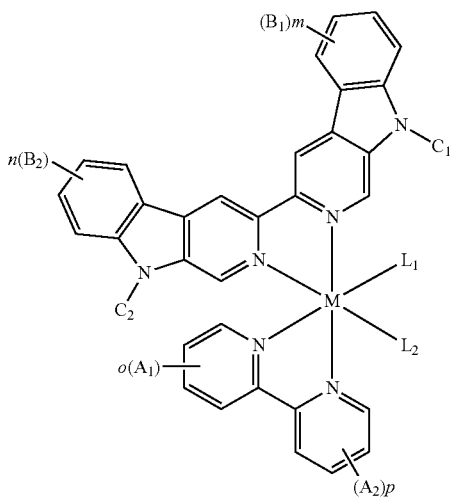

In Formula 3, $A_1$, $A_2$, $B_1$, $B_2$, M, $L_1$, $L_2$, m, n, o and p may be the same as those in Formula 1, and $C_2$ may be the same as $C_1$ in Formula 2.

Specific examples of an alkyl group, that is, a substituent used in Formulas 1 to 3, may include methyl, ethyl, propyl, isobutyl, sec-butyl, tert-butyl, pentyl, iso-amyl, ethylhexyl, hexyl, heptyl, octyl, nonyl, decyl, dodecyl, 2-ethylhexyl, etc., and at least one hydrogen atom in the alkyl group may be substituted with a halogen atom, a hydroxyl group, a nitro group, a cyano group, a silyl group (in this case, referred to as an "alkyl silyl group"), a substituted or unsubstituted amino group (—$NH_2$, —NH(R), —N(R')(R''), wherein R' and R'' each is independently a C1 to C10 alkyl group, in this case, referred to as an "alkyl amino group"), a hydrazine group, a hydrazone group, a carboxyl group, a sulfonic acid group, a phosphate group, a C1 to C20 alkyl group, a C1 to C20 halogenated alkyl group, a C1 to C20 alkenyl group, a C1 to C20 alkynyl group, a C1 to C20 heteroalkyl group, a C6 to C20 aryl group, a C6 to C20 aralkyl group, a C6 to C20 heteroaryl group or a C6 to C20 heteroaralkyl group.

Also, specific examples of an alkoxy group used as a substituent in Formulas 1 to 3 may include methoxy, ethoxy, propoxy, butoxy, pentyloxy, isobutyloxy, sec-butyloxy, pentyloxy, iso-amyloxy, hexyloxy, etc., and at least one hydrogen atom in the alkoxy group may be substituted with a substituent, like the alkyl group.

Also, an aryl group used in Formulas 1 to 3 means an aromatic system including at least one ring, and the rings may be adhered or fused together in a pendant manner. Specific examples of the aryl group may include aromatic groups such as phenyl, naphthyl, biphenyl, terphenyl anthracenyl, phenanthryl, pyrenyl, fluorenyl, chrysenyl and fluoranthenyl. At least one hydrogen atom in the aryl group may be substituted with a substituent, like the alkyl group (e.g., when substituted with an amino group, referred to as an "arylamino group", when substituted with a silyl group, referred to as an "arylsilyl group", and when substituted with an oxy group, referred to as an "aryloxy group").

Also, a heteroaryl group used as a substituent in Formulas 1 to 3 means a C3 to C30 cyclic aromatic system in which one, two or three hetero atoms are an element selected from N, O, P and S, and all of the other cyclic atoms are C. The rings may be adhered or fused together in a pendant manner. Specific examples of the heteroaryl group may include thiophene, furan, pyrrole, thiazole, oxazole, imidazole, pyridine, benzothiophene, benzofuran, benzopyrrole, benzothiazole, benzooxazole, benzoimidazole, pyrimidine, pyridazine, pyrazine, triazine, aziridine azaindolidine, indolidine, imidazole, indole, naphthalidine, quinoxaline, terpyridine, bipyridine, phenanthroline, phenazine quinoline, carbazole, indolocarbazole, etc. At least one hydrogen atom in the heteroaryl group may be substituted with the same substituent as that in the alkyl group.

Also, $L_1$ and $L_2$, functional groups used in Formulas 1 to 3 above, are ligands, and they each may be selected from the group including $H_2O$, Cl, Br, CN, NCO, NSC and NCS.

An anchoring group used in Formula 1 may be selected from the group including COOH, $PO_3H2$, $PO_4H_2$, $SO_3H_2$, $SO_4H_2$, CONHOH and a deprotonized form thereof.

As the deprotonized form, one or more terminal groups of a dye may form an anion, that is, $COO^-$, $PO^{2-}_3$, $PO^{2-}_4$, $SO^{2-}_3$, $SO^{2-}_4$, or $CONHO^-$. Herein, the terminal group of the dye may form a salt in combination with a cation. The cation may be selected from the group including ammonium, phosphonium, sulfonium, imidazolium, pyrrolidonium and pyridinium although it is not particularly limited thereto.

Above described substituents may be substituted or unsubstituted again although not described.

Specific examples of an organic metal dye that includes a fused heterocyclic derivative according to an embodiment of the present invention, represented by Formulas 1 to 3, may include compounds represented by Formulas 4 to 87 below, but the present invention is not limited to the exemplified compounds.

[Formula 4]

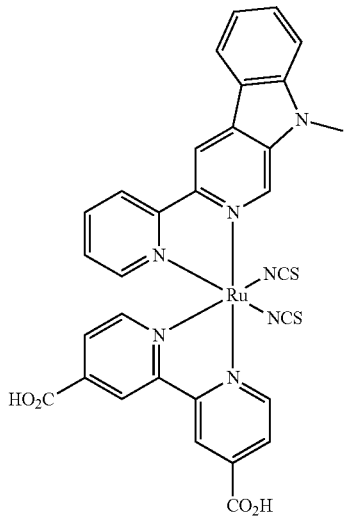

[Formula 5]

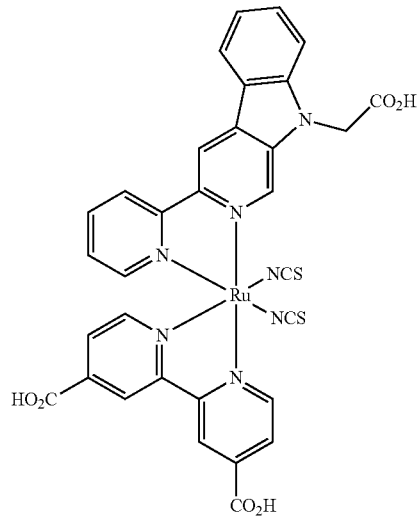

[Formula 6]

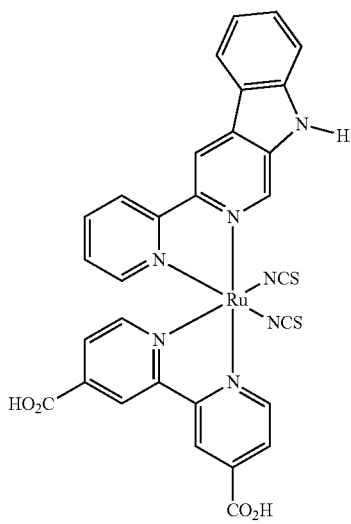

[Formula 7]

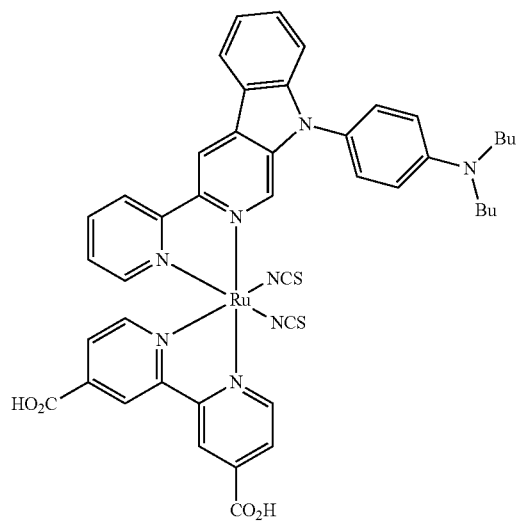

[Formula 8]

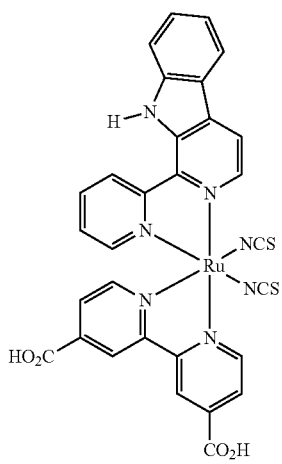

[Formula 9]

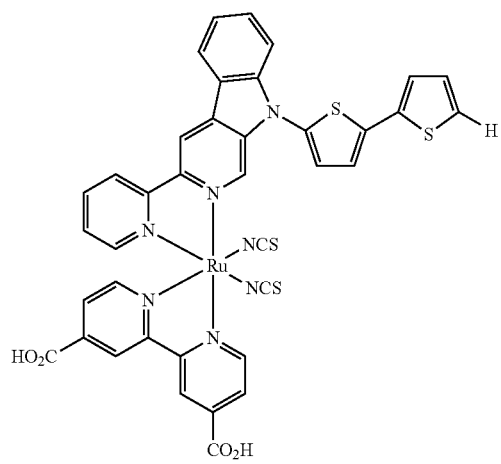

[Formula 10]
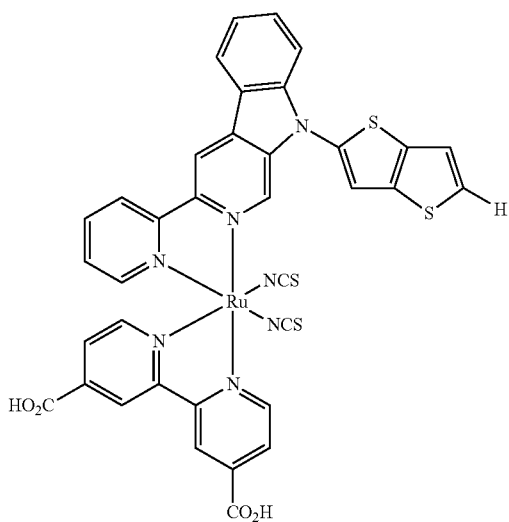
[Formula 11]
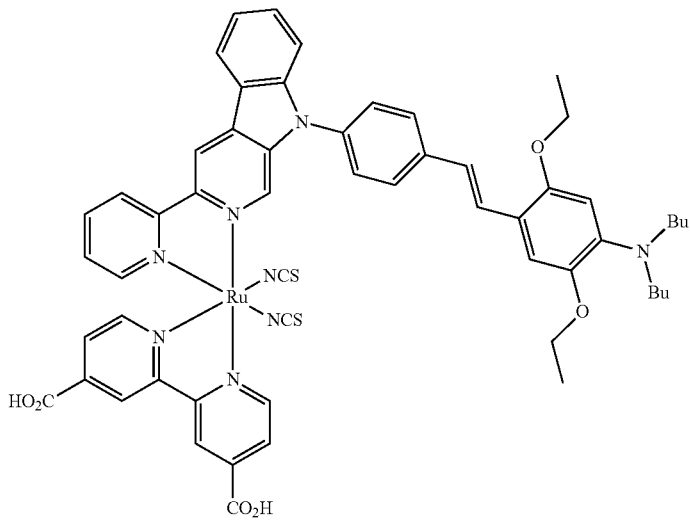
[Formula 12]
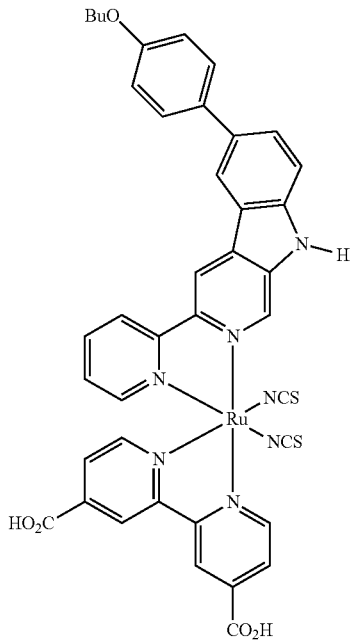
[Formula 13]
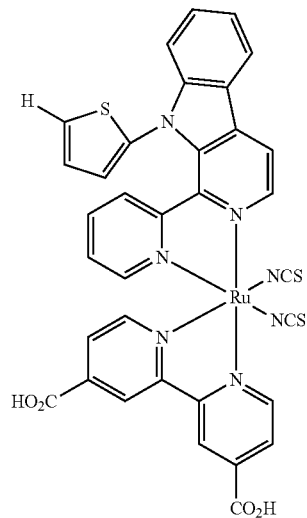

[Formula 14]
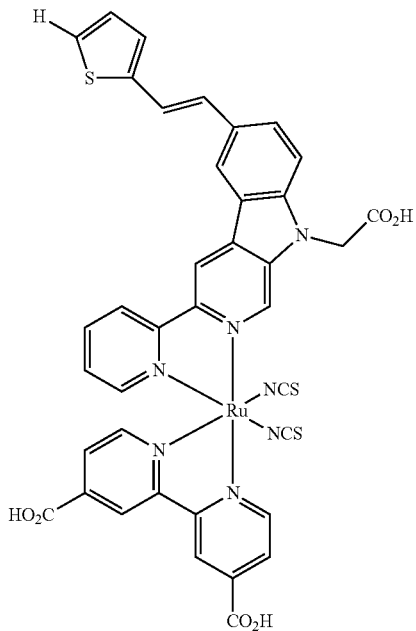
[Formula 15]
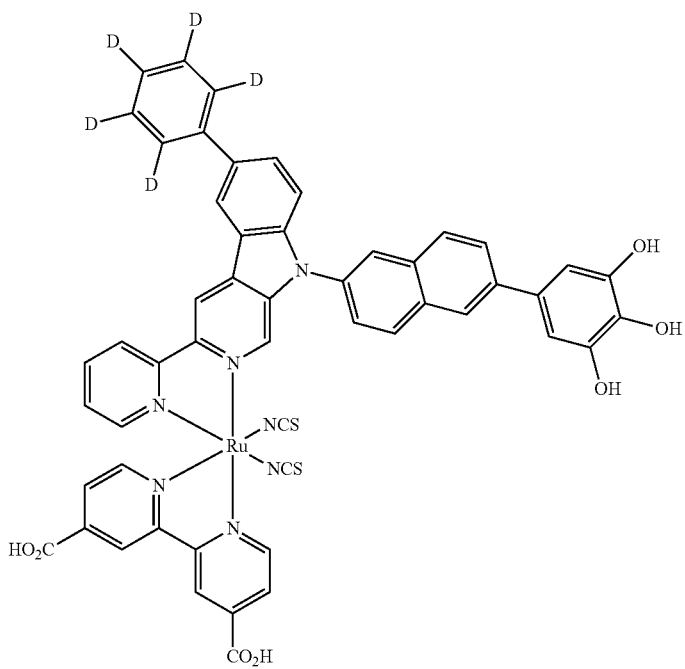

[Formula 16]
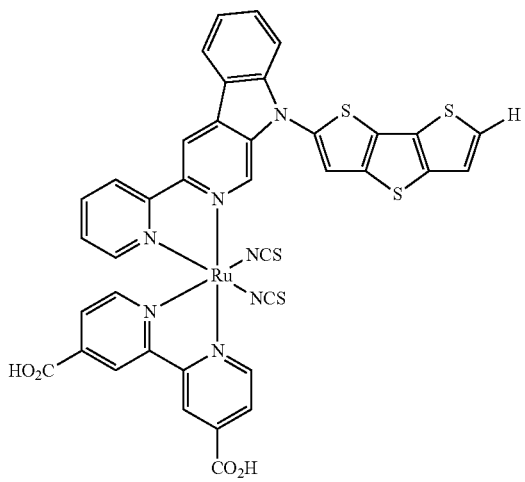
[Formula 17]
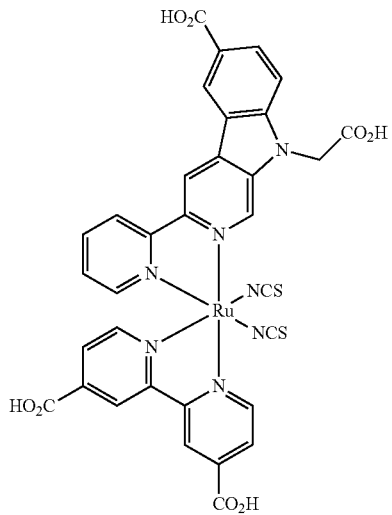
[Formula 18]
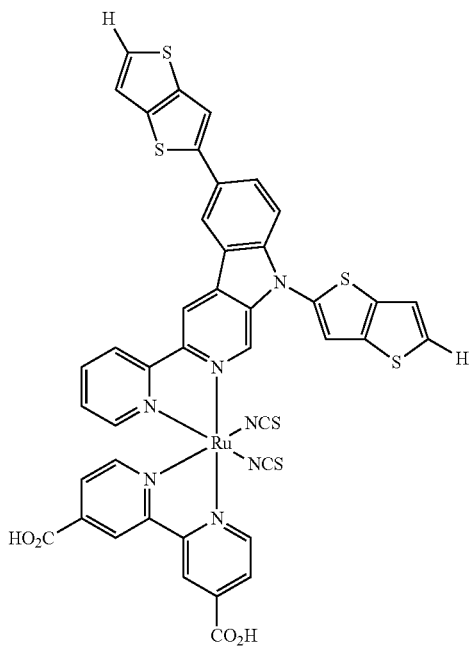
[Formula 19]
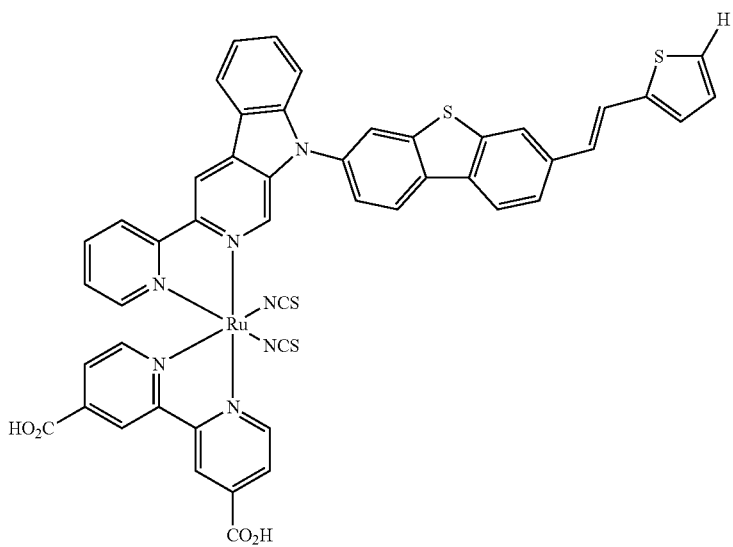

-continued
[Formula 20]
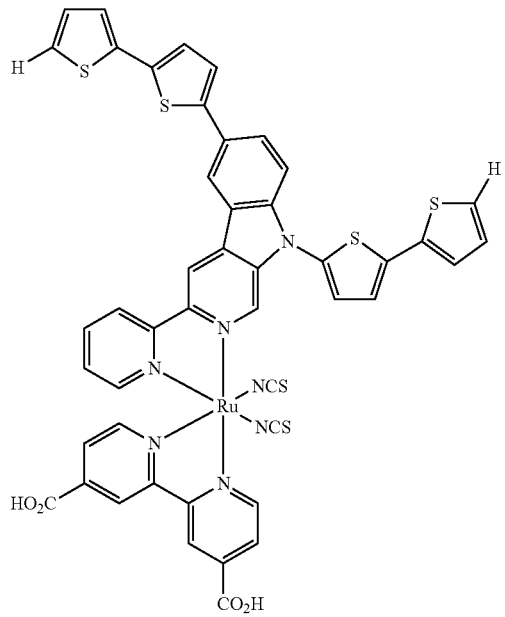
[Formula 21]
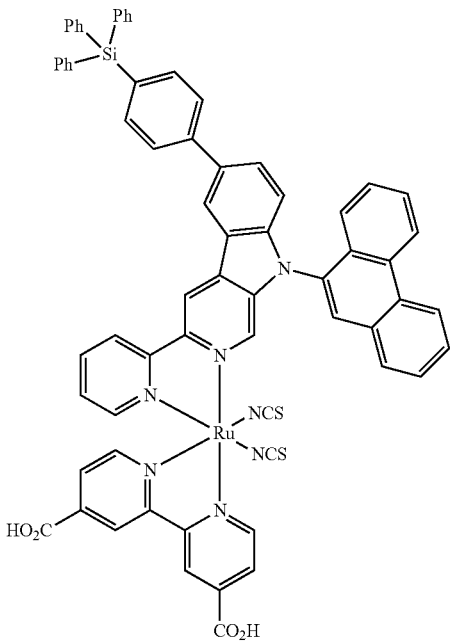
[Formula 22]
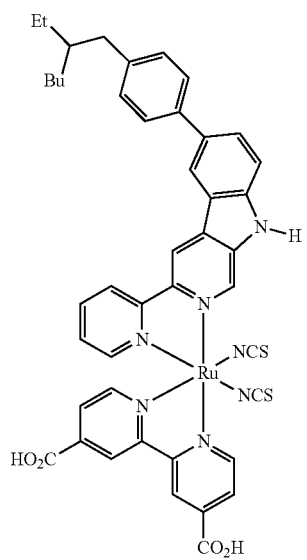
[Formula 23]
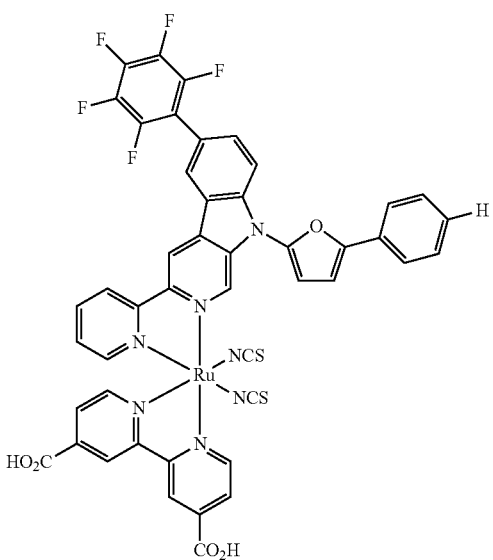

[Formula 24]
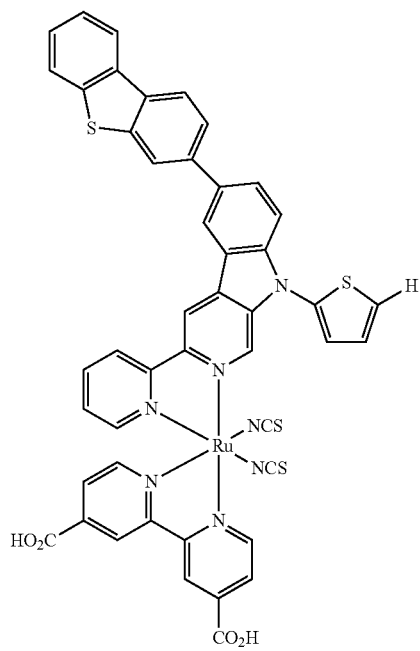
[Formula 25]
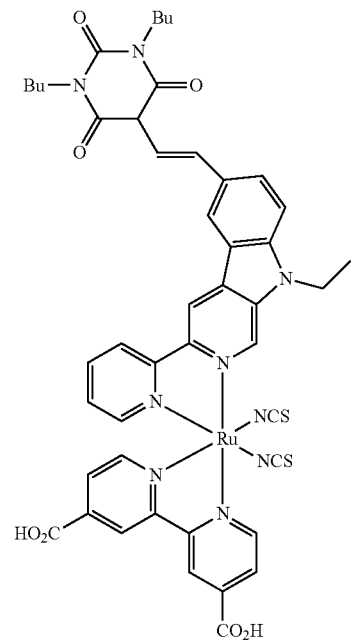
[Formula 26]
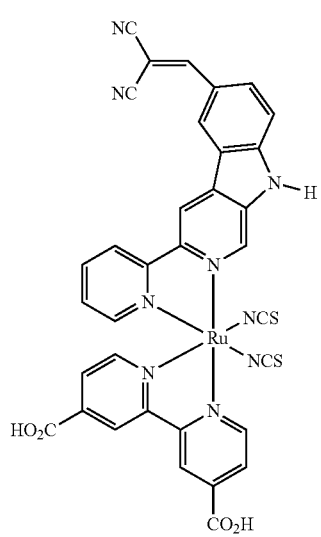
[Formula 27]
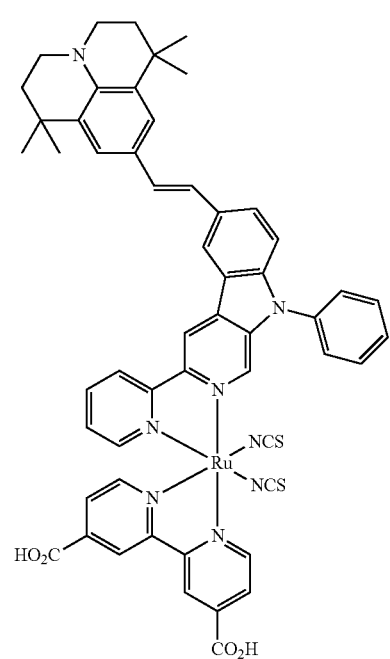

-continued
[Formula 28]
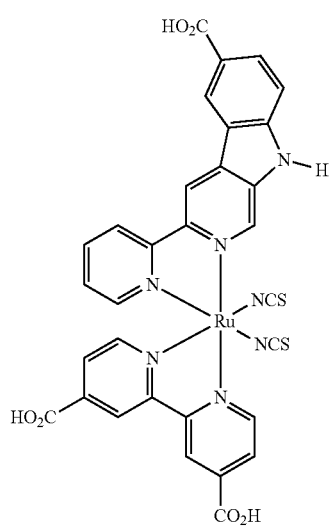
[Formula 29]
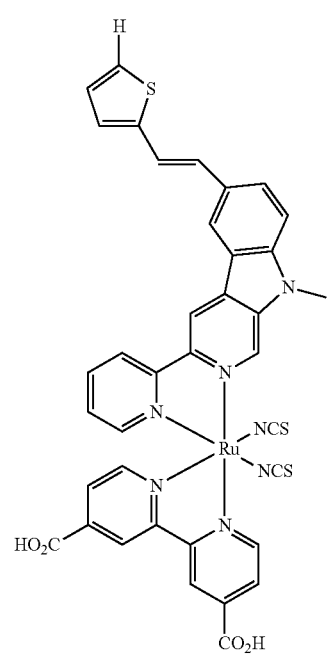
[Formula 30]
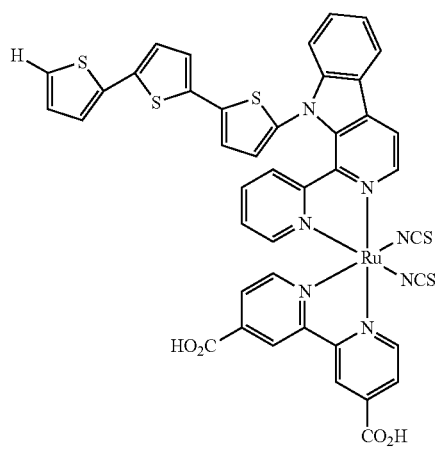
[Formula 31]
[Formula 32]
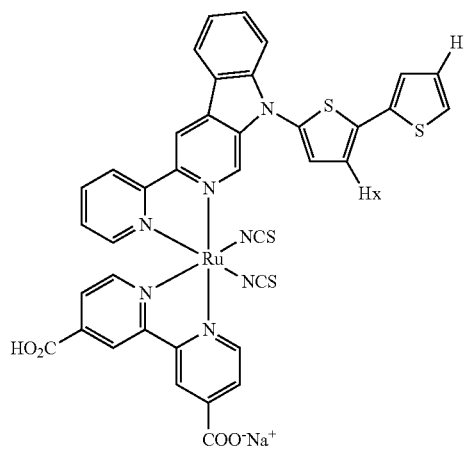
[Formula 33]
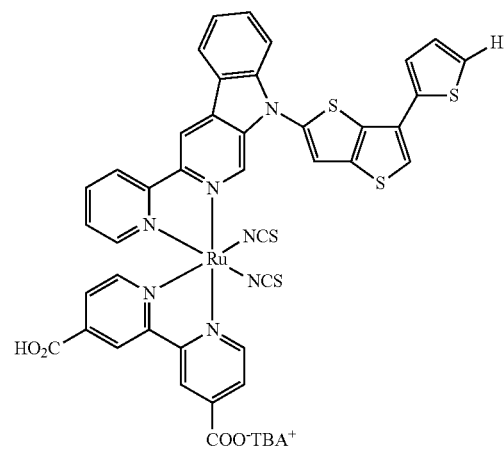

-continued
[Formula 34]
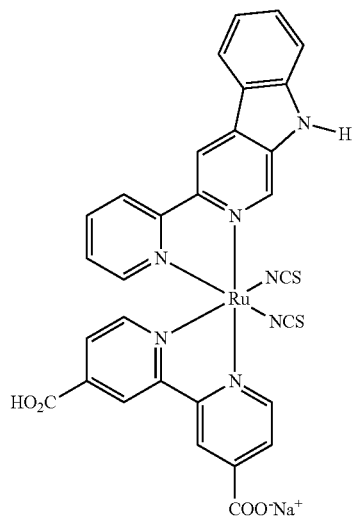
[Formula 35]
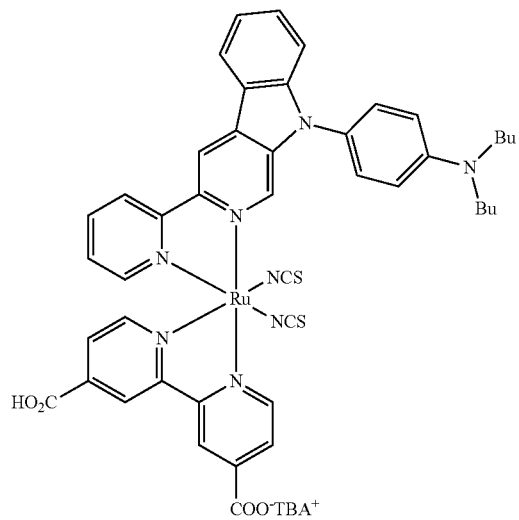
[Formula 36]
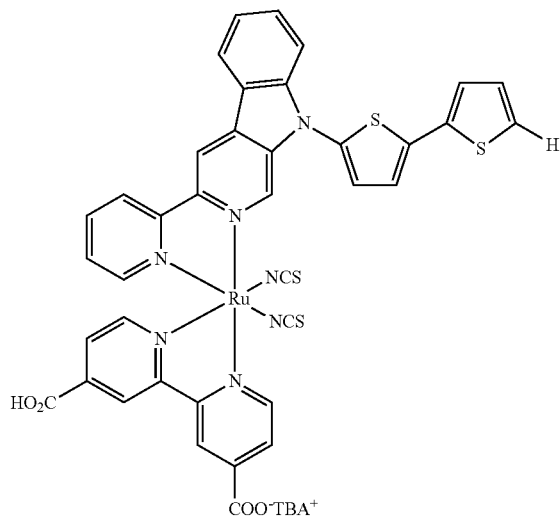
[Formula 37]
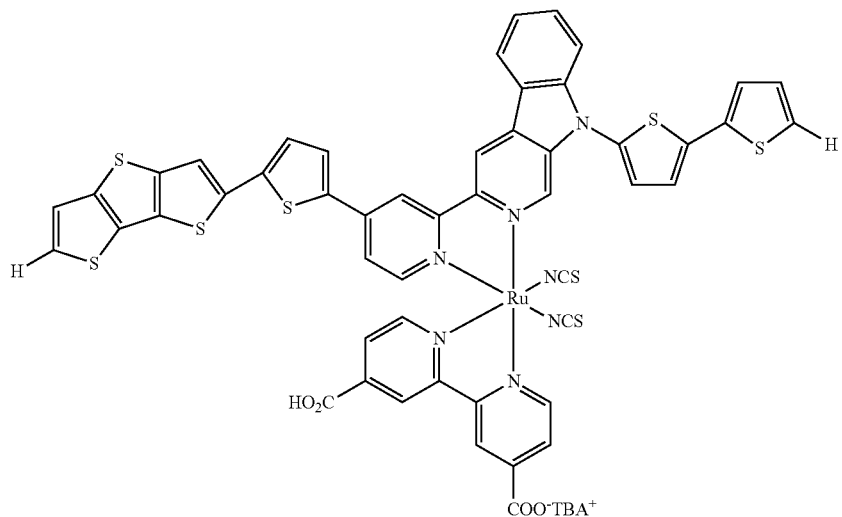

-continued
[Formula 38]
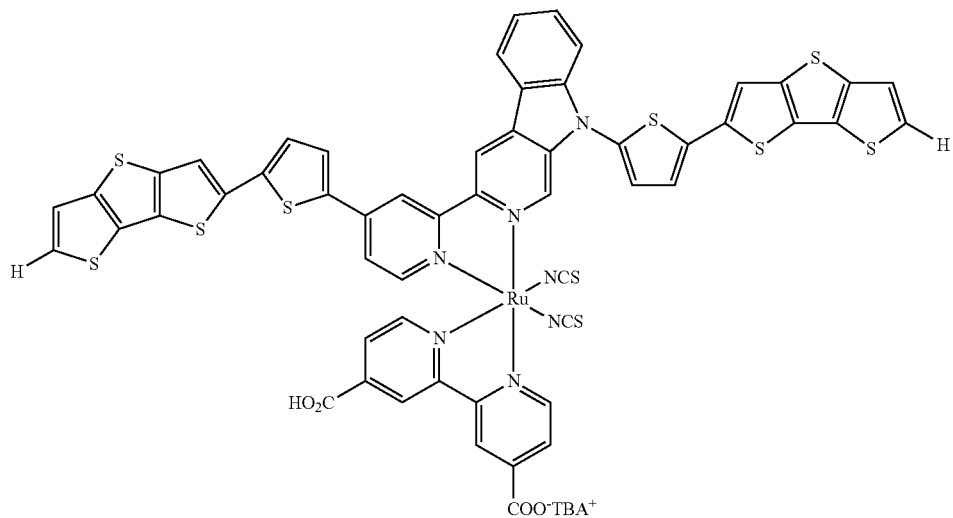
[Formula 39]
[Formula 40]
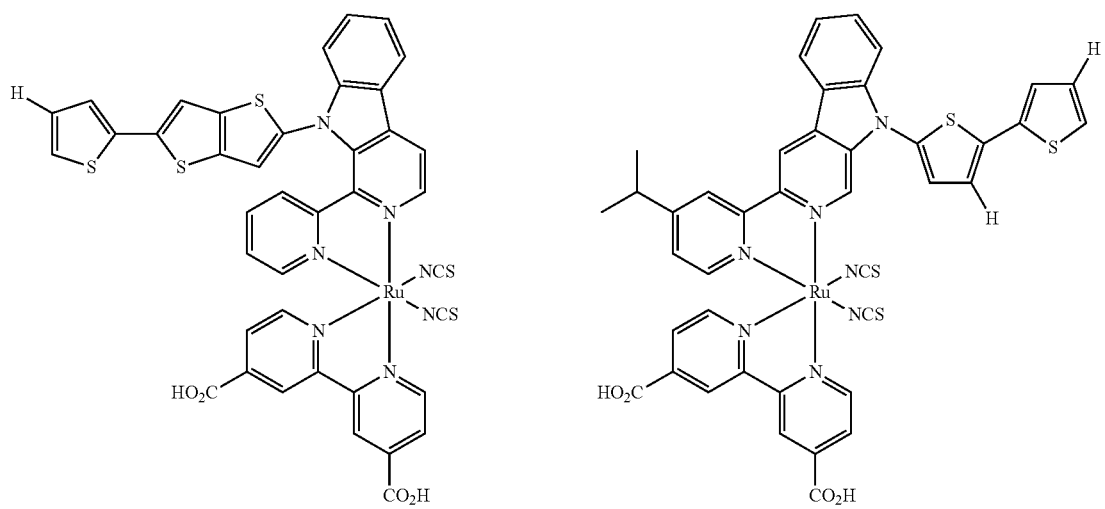
[Formula 41]
[Formula 42]
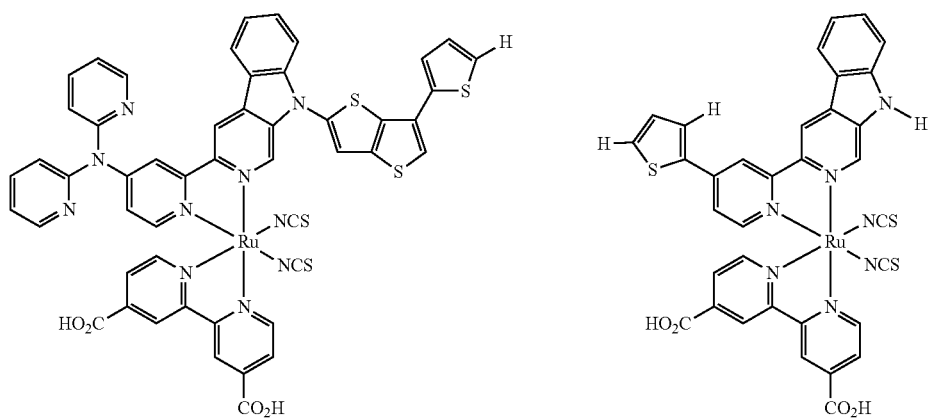

-continued
[Formula 43]
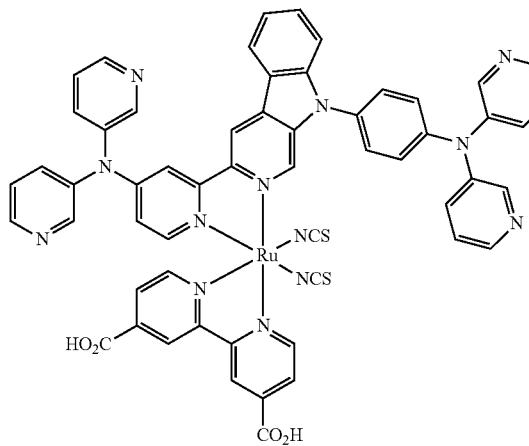
[Formula 44]
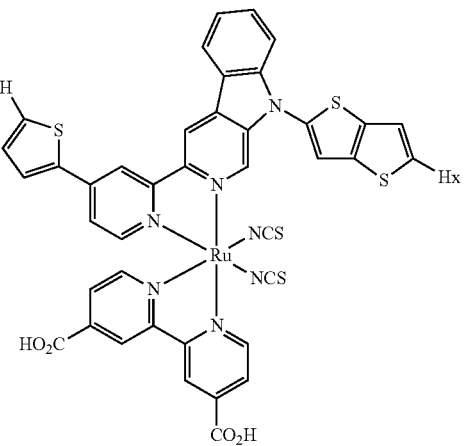
[Formula 45]
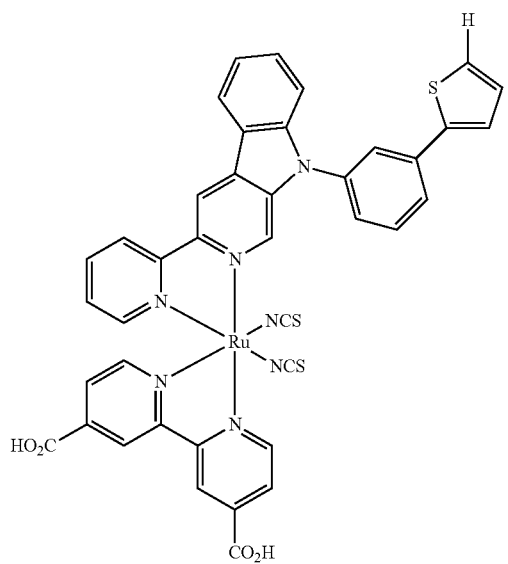
[Formula 46]
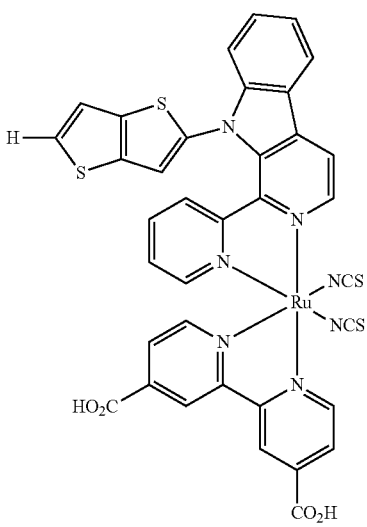
[Formula 47]
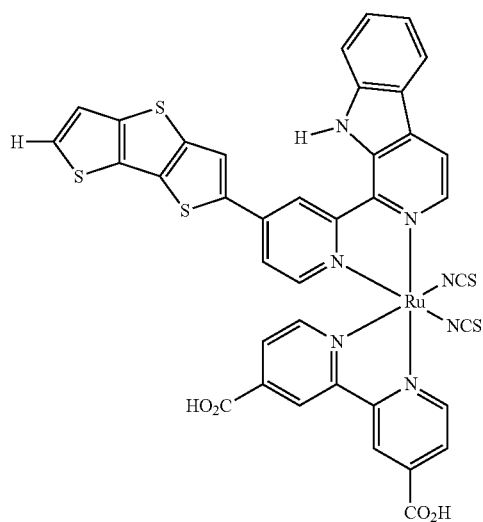
[Formula 48]
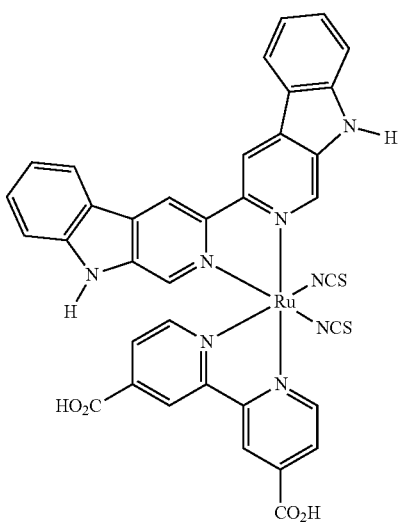

-continued
[Formula 49]
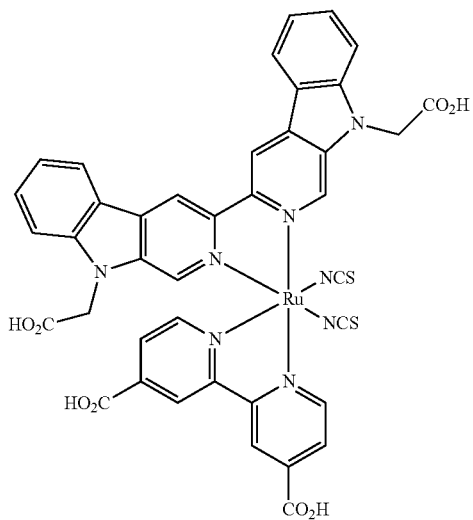
[Formula 50]
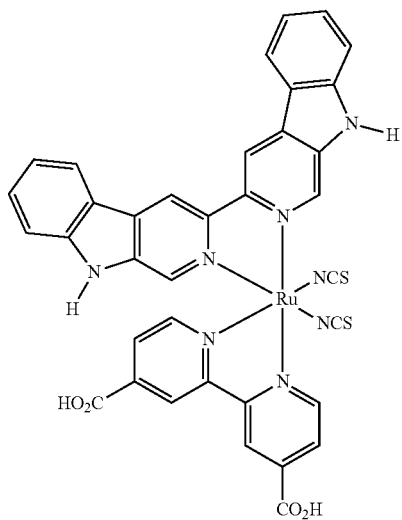
[Formula 51]
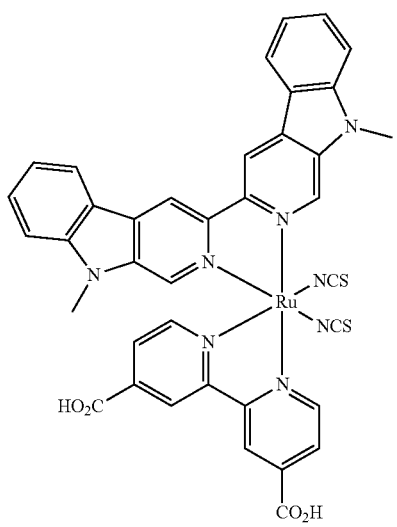
[Formula 52]
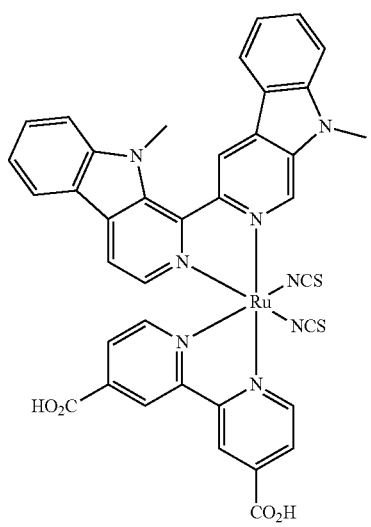
[Formula 53]
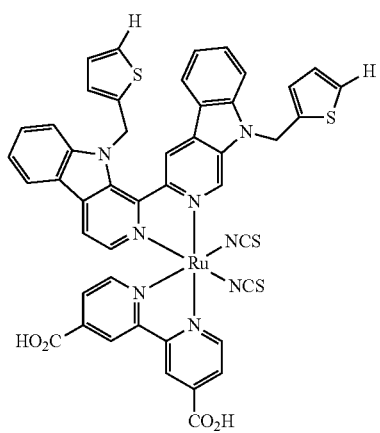
[Formula 54]
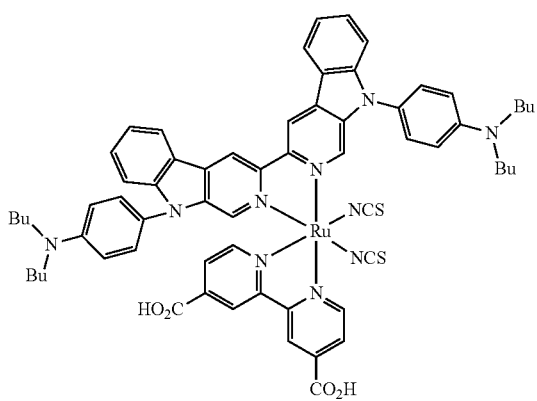

[Formula 55]
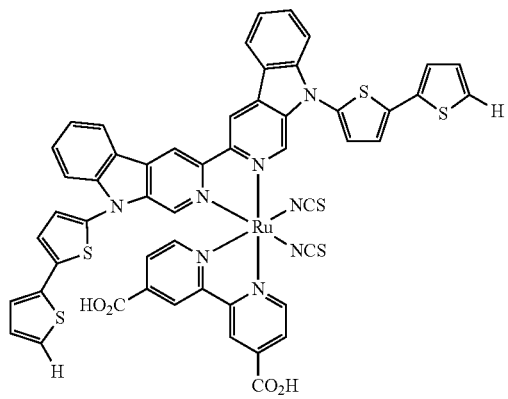
[Formula 56]
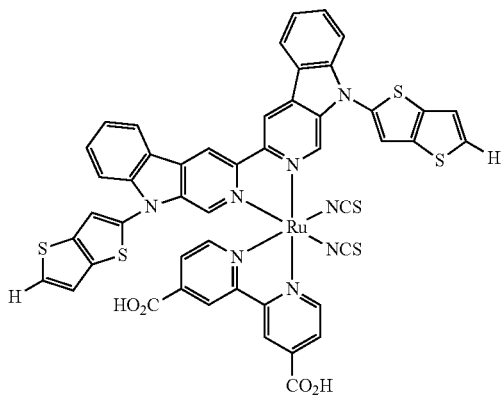
[Formula 57]
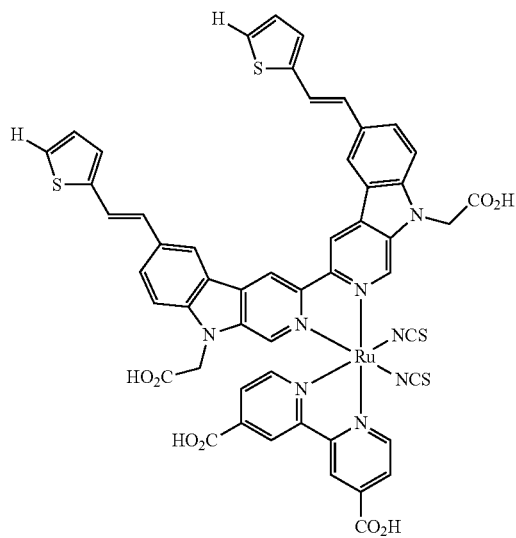
[Formula 58]
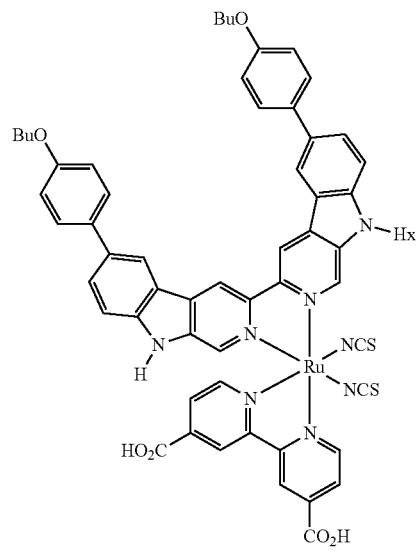
[Formula 59]
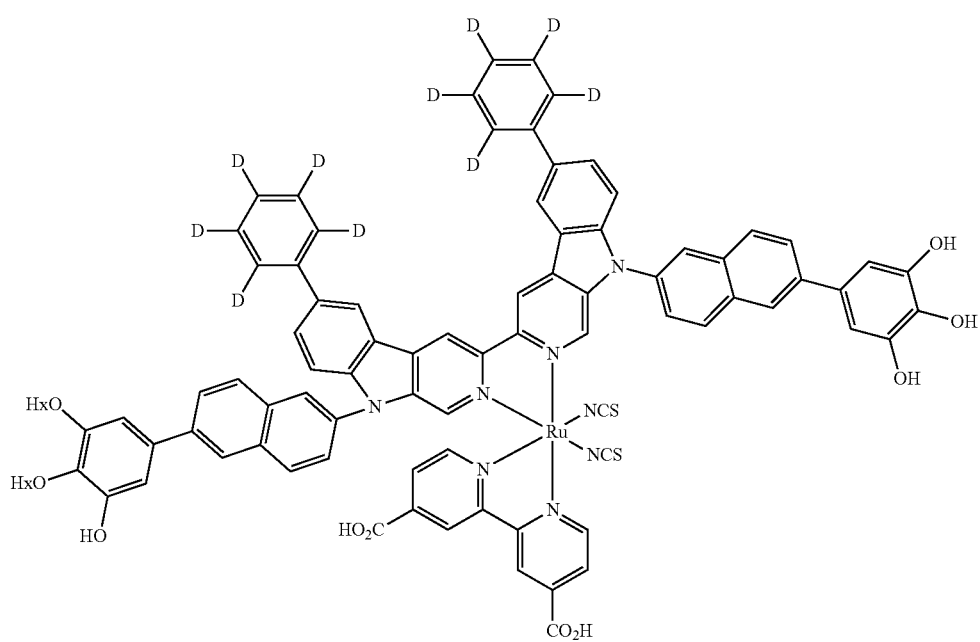

-continued
[Formula 60]
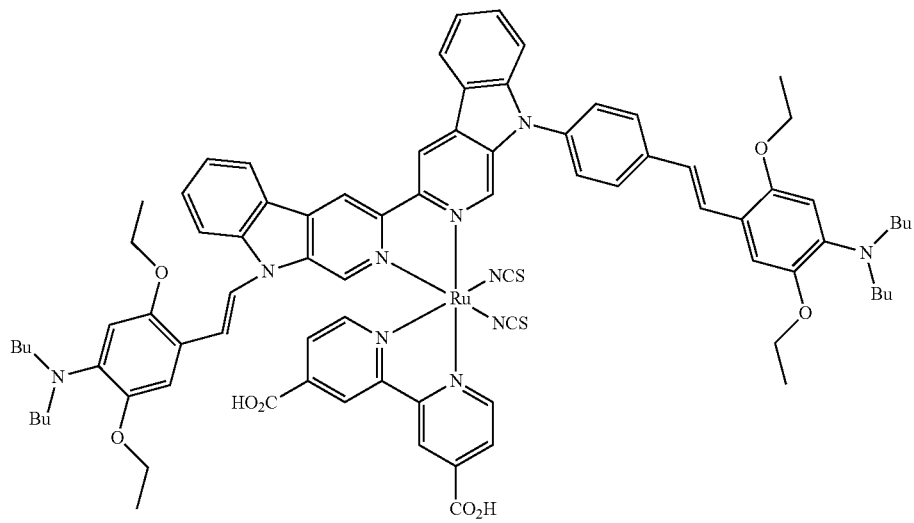
[Formula 61]
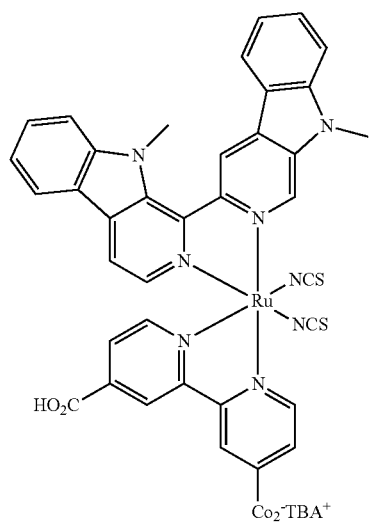
[Formula 62]
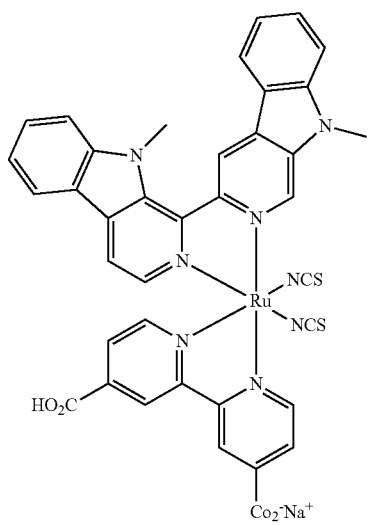
[Formula 63]
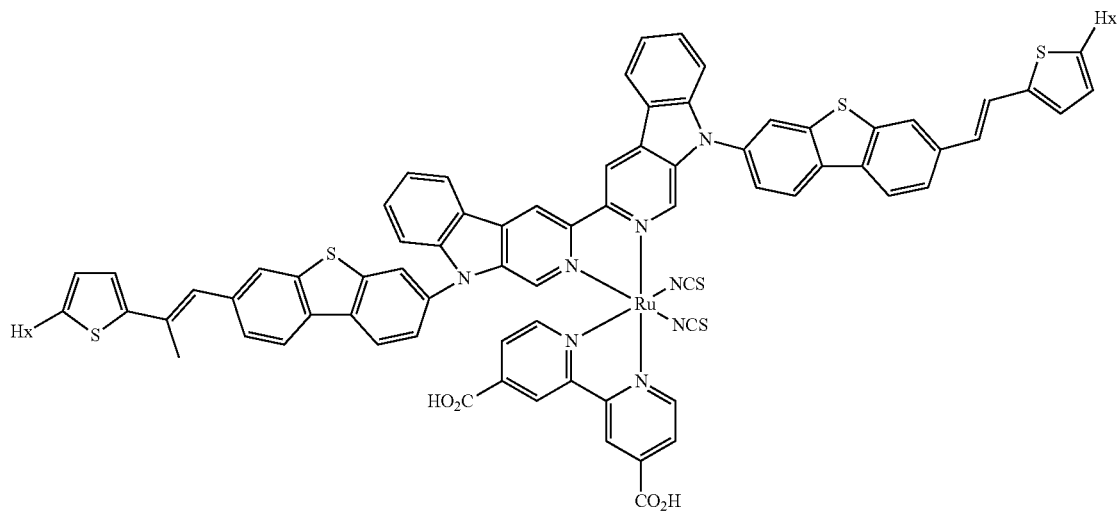

[Formula 64]
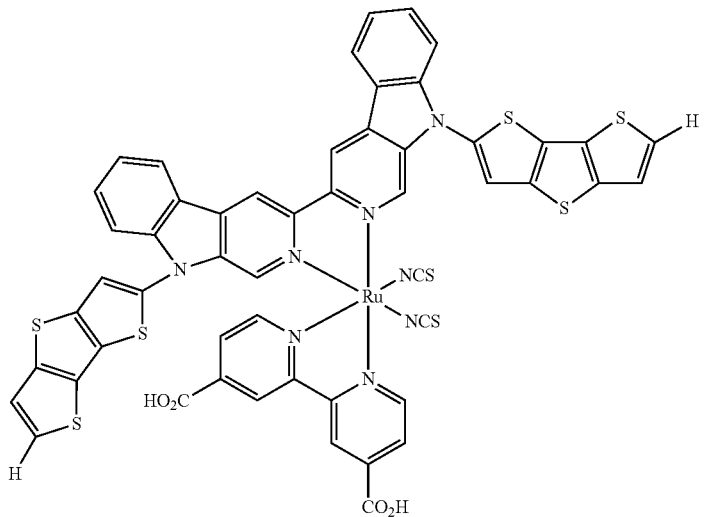
[Formula 65]
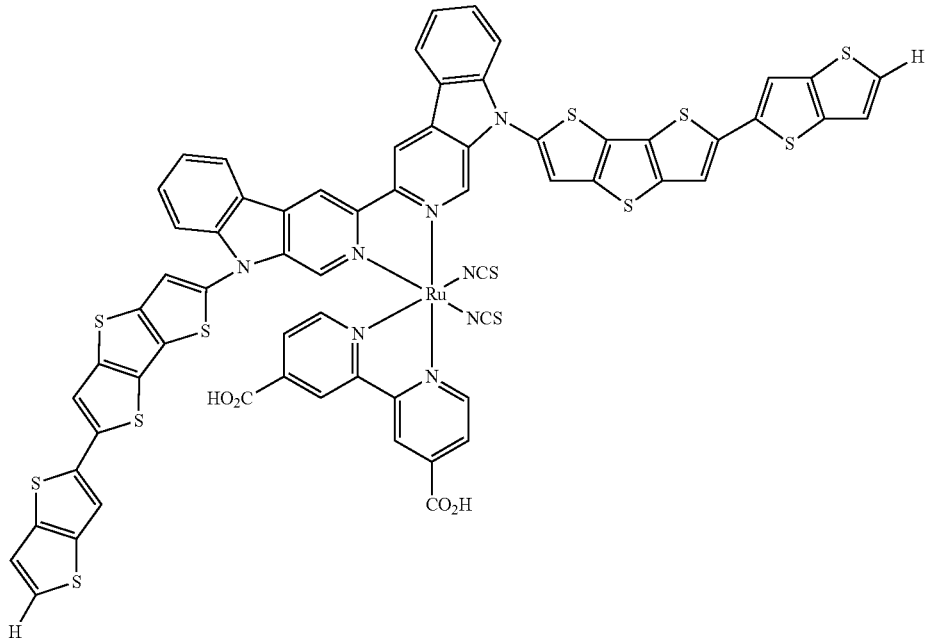

[Formula 66]
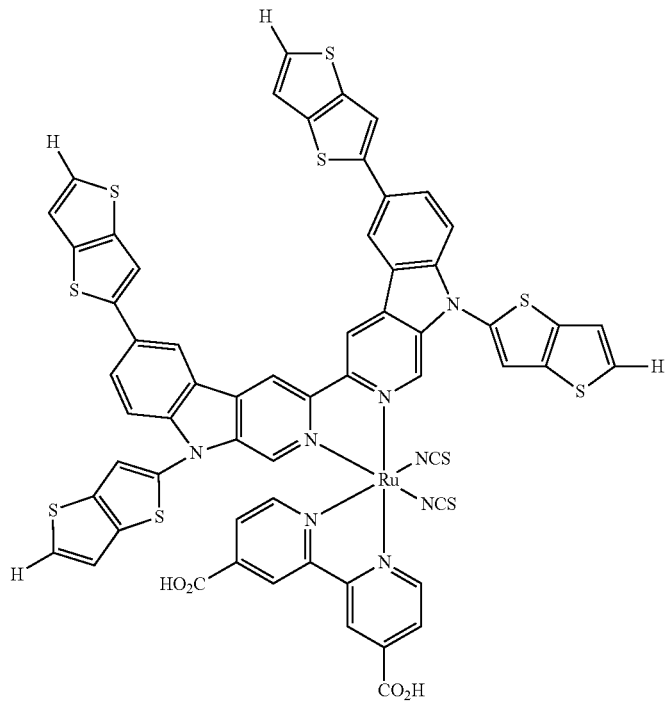
[Formula 67]
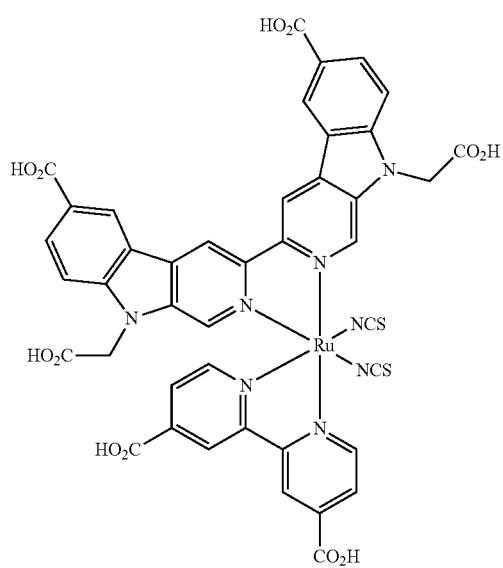

[Formula 68]
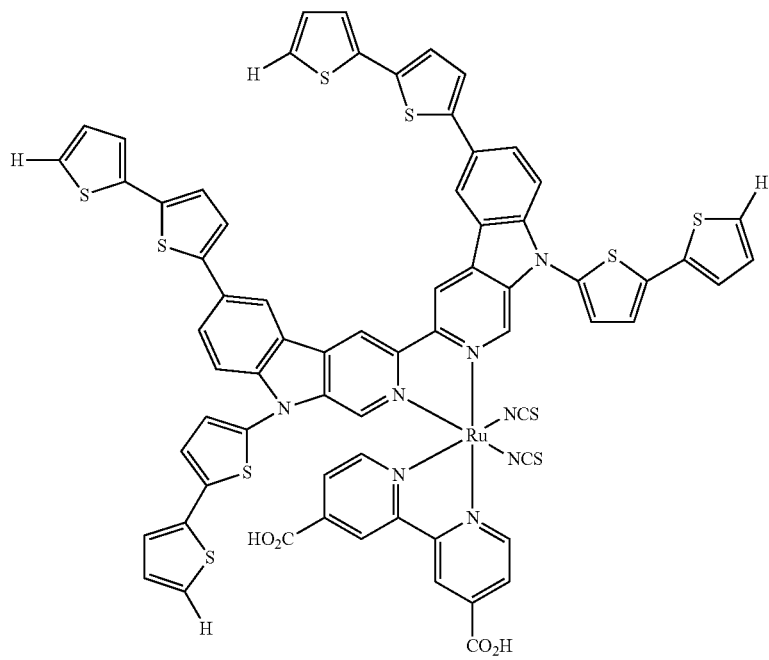
[Formula 69]
[Formula 70]
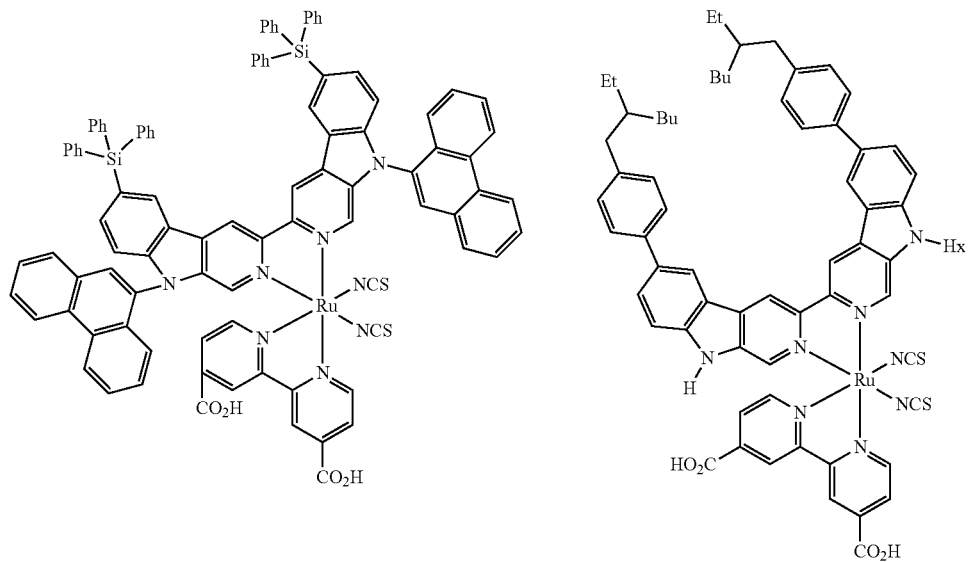

-continued
[Formula 71]
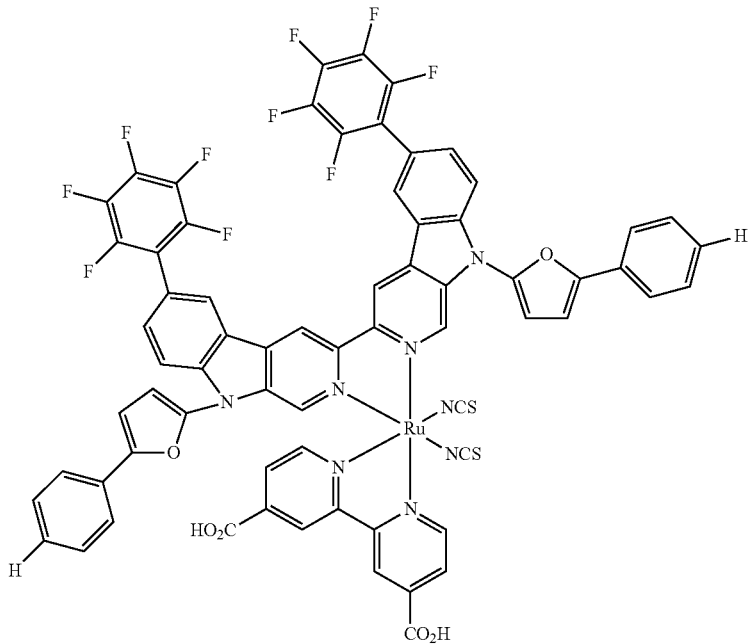
[Formula 72]
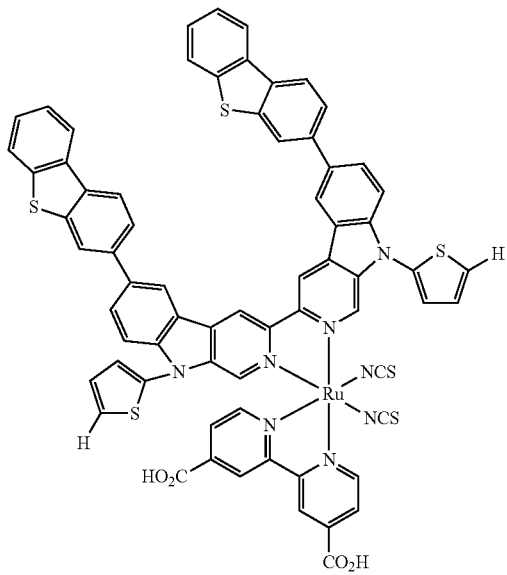
[Formula 73]
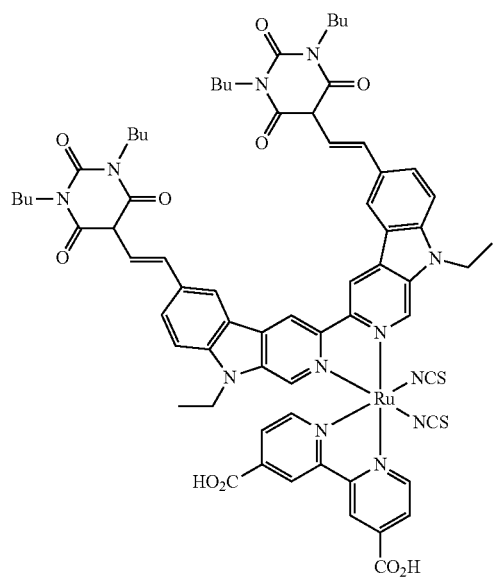

-continued
[Formula 74]
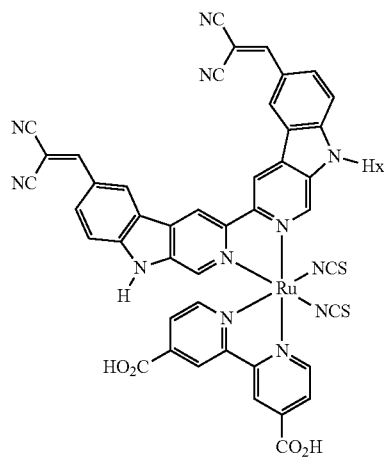
[Formula 75]
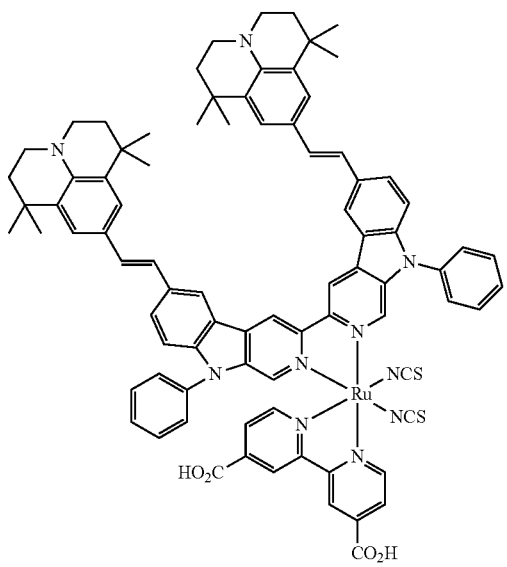
[Formula 76]
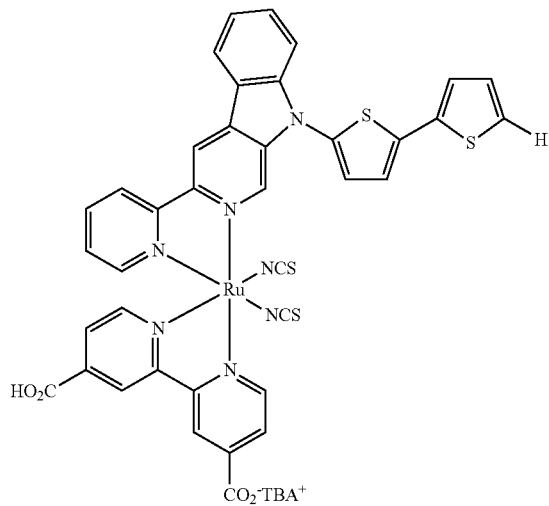
[Formula 77]
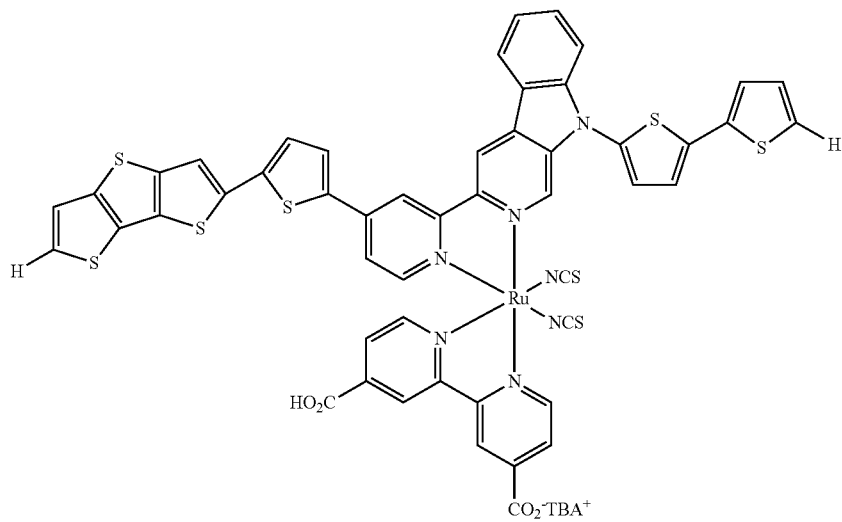

-continued
[Formula 78]
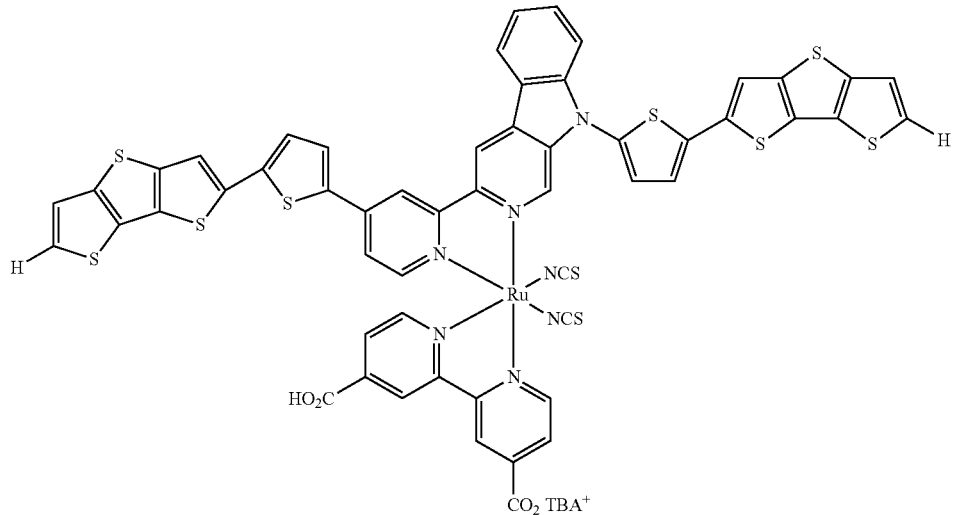
[Formula 79]
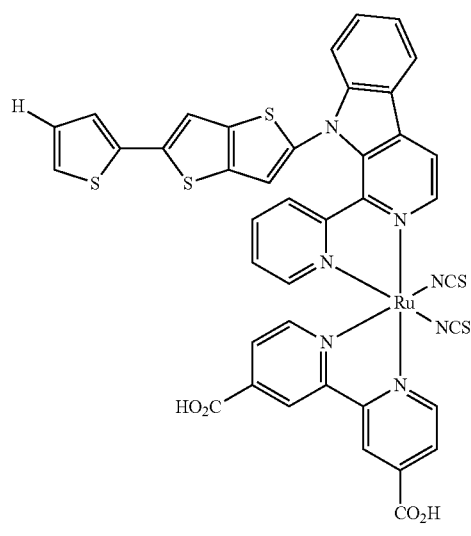
[Formula 80]
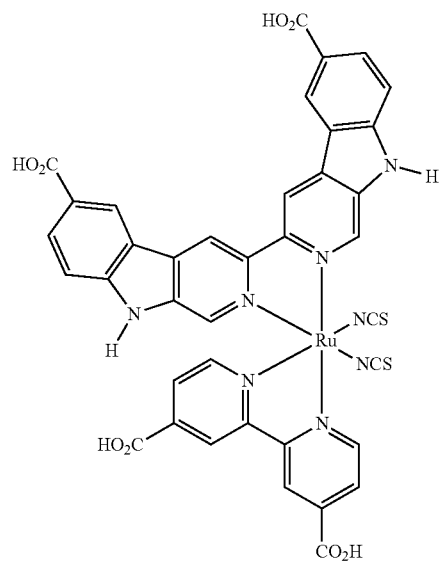

[Formula 81]
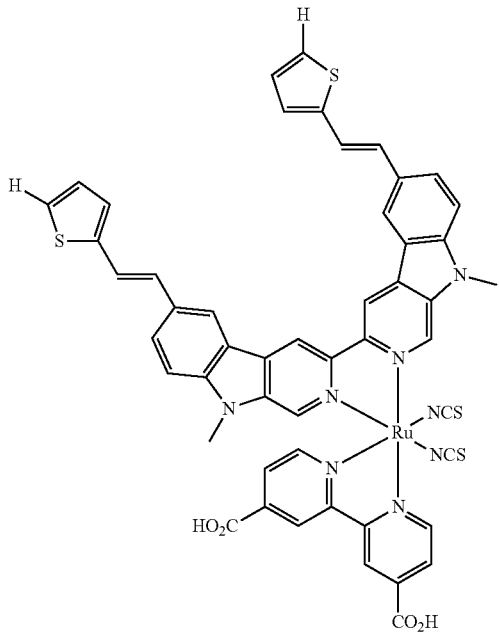
[Formula 82]
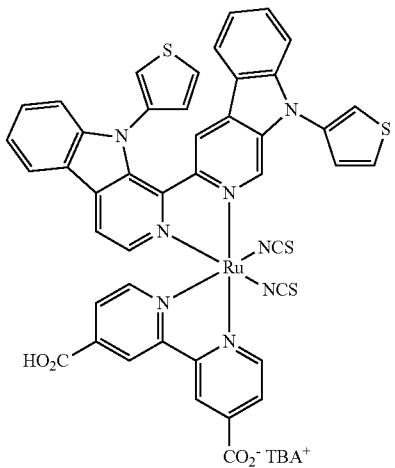
[Formula 83]
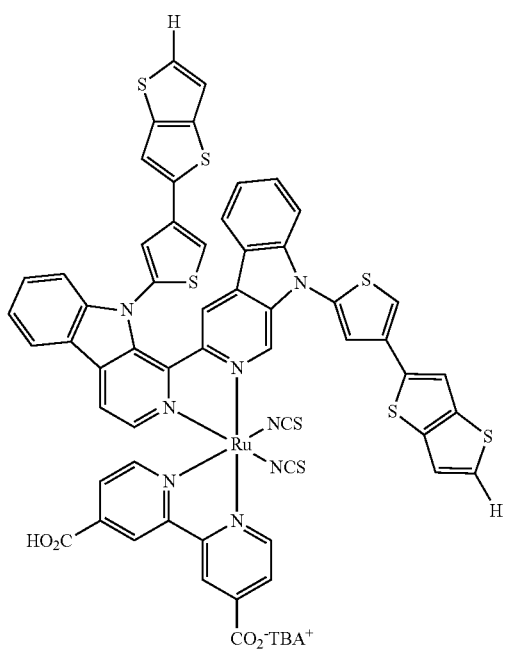

[Formula 84]

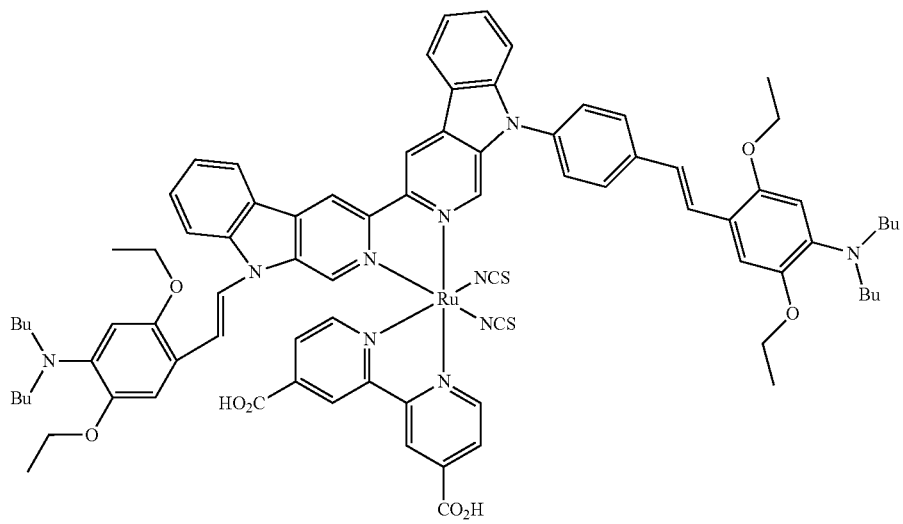

[Formula 85]

[Formula 86]

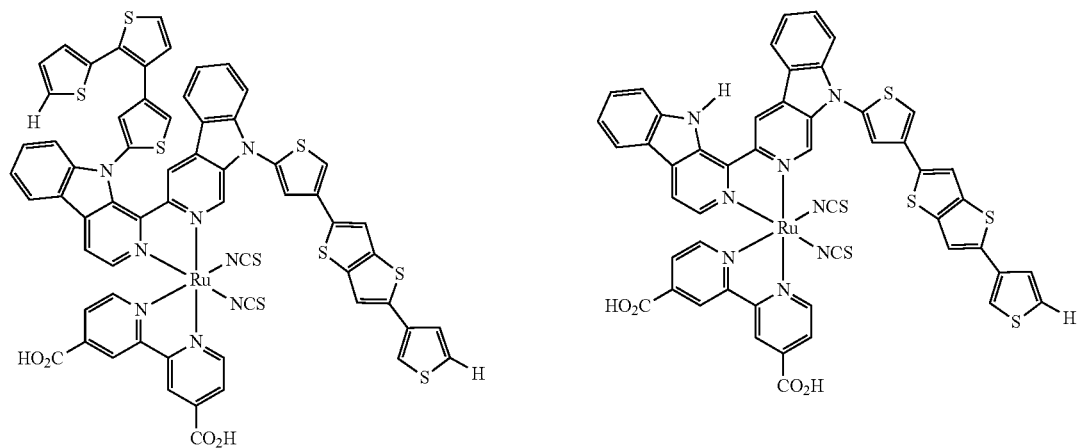

[Formula 87]

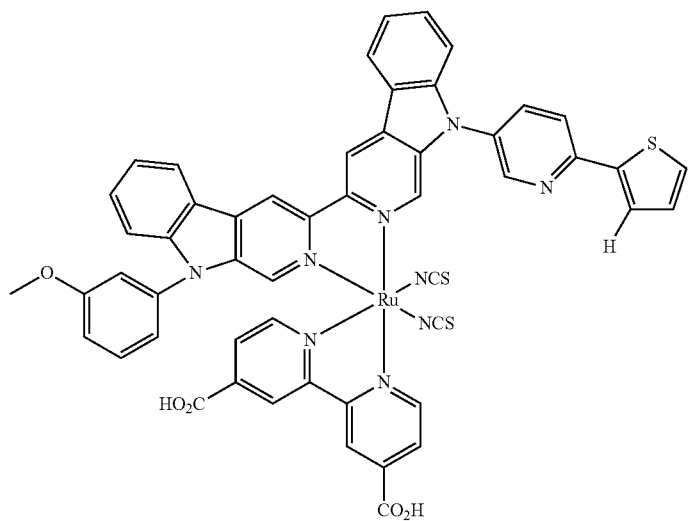

Unlike a silicon solar cell, a dye-sensitized solar cell is a photoelectrochemical solar cell that includes photo-sensitized dye molecules capable of forming an electron-hole pair by absorbing visible light and transition metal oxide for transferring generated electrons, as main materials. The photoelectric conversion efficiency of the dye-sensitized solar cell is in proportion to the amount of electrons generated by sunlight absorption. Thus, in order to improve the efficiency, the amount of generated electrons can be increased by an increase in sunlight absorption or an increase in dye adsorption. Otherwise, in order to improve the efficiency, it is possible to inhibit generated excited electrons from being annihilated through electron-hole recombination.

The inventors of the present invention have developed an organic metal dye represented by Formulas 1 to 3, including a fused hetero cycle, in order to achieve a higher light absorptivity.

Meanwhile, the inventors have developed a dye-sensitized solar cell, in which the dye-sensitized solar cell includes: a first electrode; a light absorbing layer formed on any one surface of the first electrode; a second electrode that is disposed opposingly to the first electrode having the light absorbing layer formed thereon; and an electrolyte filled up in a space between the first electrode and the second electrode. Herein, in the dye-sensitized solar cell, the organic metal dye represented by Formulas 1 to 3 may be supported by oxide semiconductor fine particles of the light absorbing layer.

Hereinafter, a dye-sensitized solar cell using the organic metal dye represented by Formulas 1 to 3 will be exemplified, but the use of the organic metal dye is not limited thereto. For example, the organic metal dye may be used in various photoelectric elements such as a photoelectric tube and a photomultiplier using a photoemissive surface, a photoelectric cell using an internal photoelectric effect, a photovoltaic cell, a photodiode or a phototransistor, a photo sensor. Herein, the photoelectric elements basically have the same or substantially the same basic structure as that of the dye-sensitized solar cell to be described later, but according to the use, components may be partially added, omitted, modified, or changed.

FIG. 1 shows a layered structure of a dye-sensitized solar cell according to an embodiment of the present invention.

The dye-sensitized solar cell according to an embodiment of the present invention includes: a first electrode 101; a light absorbing layer 102 formed on any one surface of the first electrode 101; a second electrode 104 that is disposed opposingly to the first electrode 101 having the light absorbing layer 102 formed thereon; and an electrolyte 103 intervened in a space between the first electrode 101 and the second electrode 104.

The first electrode 101 is any one of two electrodes of a solar cell, and may be a conductive substrate.

The surface of the conductive substrate 101 may be conductive. Also, as the conductive substrate 101, a conductive metal oxide (such as tin oxide) obtained by coating indium, fluorine, or antimony on the surface of glass or transparent polymer material, or a metal thin film of steel, silver, gold or the like may be used.

The light absorbing layer 102 includes a porous oxide semiconductor fine particle film formed on the conductive substrate 101, and an organic metal dye adsorbed on the oxide semiconductor fine particle film.

The porous oxide semiconductor fine particle film includes oxide semiconductor fine particles, and is formed on the conductive substrate 101. The oxide semiconductor fine particle film may be specifically made of an oxide of titanium, tin, zinc, tungsten, zirconium, gallium, indium, yttrium, niobium, tantalum, or vanadium. The porous oxide semiconductor fine particle film may be used alone, or in combination, and also may be coated on the surface of a semiconductor. Also, the porous oxide semiconductor fine particles may have an average particle diameter of 1 to 500 nm, in which particles of a large particle diameter and a small particle diameter may be used in combination, or used in a multi-layer structure. When the porous oxide semiconductor fine particle film is used in a multi-layered structure, a recombination inhibiting layer of a porous oxide semiconductor film with a small particle diameter (a porosity of 0 to 10%) is formed on the first conductive substrate 101, and a porous oxide semiconductor film layer with a large particle diameter (a porosity of 40 to 60%) is formed on the electron recombination inhibiting layer.

The porous oxide semiconductor fine particle film may be formed by coating a paste containing semiconductor fine particles on the conductive substrate 101, followed by drying, hardening and firing. In this method, a semiconductor-containing paste may be dispersed in various solvents such as water, ethanol, etc. so as to form slurry, and then the slurry is coated on the substrate. The substrate coated with the slurry is fired at 400 to 600° C. for about 4 hours. In the dye-sensitized solar cell according to an embodiment of the present invention, the porous oxide semiconductor fine particle film on the substrate may have a thickness of 1 to 2,000 nm, or a thickness of 1 to 500 nm.

On the formed semiconductor fine particle film, a photo sensitized organic metal dye represented by Formulas 1 to 3 is adsorbed. A method of adsorbing the photo sensitized organic metal dye represented by Formulas 1 to 3 on the semiconductor fine particle film is not particularly limited. Specifically, the dye may be adsorbed by supporting the oxide semiconductor fine particle film by a solution obtained by dissolving the compound represented by Formulas 1 to 3 in its soluble solvent, or a dispersion obtained by dispersing the dye in a solvent.

Herein, the concentration of the dye used in the solution or the dispersion may be appropriately adjusted according to the characteristic of the dye. Also, after the semiconductor fine particle film is supported, a time required for adsorbing the dye on the porous oxide is about 1 to 48 hours. A solvent used for dissolving or dispersing the dye may be ethanol, water, acetonitrile, acetone, dimethylformaldehyde or the like, but the present invention is not limited thereto.

In the dye to be adsorbed on the oxide, the anchoring group may be selected from the group including COOH, $PO_3H2$, $PO_4H_2$, $SO_3H_2$, $SO_4H_2$, CONHOH and a deprotonized form thereof. As the deprotonated form, one or more terminal groups of a dye may form an anion, such as $COO^-$, $PO^{2-}_3$, $PO^{2-}_4$, $SO^{2-}_3$, $SO^{2-}_4$, or $CONHO^-$, and in this case may form a salt in combination with a cation. The cation may be selected from the group including ammonium, phosphonium, sulfonium, imidazolium, pyrrolidonium and pyridinium although it is not particularly limited thereto.

The second electrode 104 is disposed opposingly to the first electrode 101, and includes the same or similar conductive electrode and the same or similar conductive layer as the first electrode 101. The conductive layer may be made of a carbon material (such as carbon black, carbon nanotube), or platinum. One or both of the first electrode 101 and the second electrode 104 may be transparent.

Electrolyte layer 103 is sealed by a partition wall intervened between the first electrode 101 and the second electrode 104. As a redox electrolyte used for the electrolyte layer 103, a halogen redox electrolyte including a halogen compound using a halogen ion as a counter-ion, and halogen molecules, a metal redox electrolyte of ferrocyanide, ferrocene-ferricinium ion, or metal complex (such as cobalt complex), an organic redox electrolyte of alkyl thiol-alkyl disulphide, viologen dye, or hydroquinone-quinone, or the like may be used. Also, a halogen redox electrolyte may be used.

Also, a molecular iodine may be used. Also, as the halogen compound using a halogen ion as a counter ion, a halogenated metal salt (such as LiI, NaI, KI, $CaI_2$, CuI, or the like), an organic ammonium salt of halogen (such as tetraalkyl ammonium iodide, imidazolium iodide, pyridium iodide or the like), or $I_2$ may be used.

Specific examples of the electrolyte layer 103 are as follows, but the present invention is not limited thereto.

The electrolyte layer 103 may include an iodine-based redox liquid electrolyte, e.g., an electrolyte solution of $I_3^-/I^-$ obtained by dissolving 1-vinyl-3-hexyl-3-immidazolium iodide, 0.1M LiI, 40 mM I2 (Iodine), and 0.2M tert-butyl pyridine in 3-methoxypropionitrile.

EXAMPLE

Hereinafter, the present invention will be described in more detail with reference to Synthesis Examples and Comparative Test Examples. However, the following Synthesis Examples and Comparative Test Examples are only for illustrative purposes and are not intended to limit the scope of the invention.

Synthesis Example 1

Preparation of a Compound Represented by Formula 6

1) Synthesis of a Compound Represented by Formula 1-a
According to Reaction Scheme 1 below, a compound represented by Formula 1-a was synthesized.

[Reaction Scheme 1]

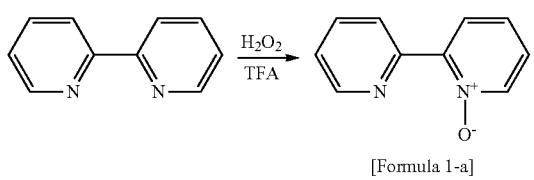

[Formula 1-a]

A 5 L round-bottom flask was charged with 119.5 g of trifluoroacetic acid (1.05 mol), and slowly added with 250 g of 2,2'-bipyridine (1.59 mol). At room temperature, 275 g of hydrogen peroxide was slowly added thereto, followed by stirring for 4 hours. The resultant product was added with a sodium hydroxide aqueous solution until pH reached 9 to 11, and extracted with methylene chloride. Then, an organic layer was separated. After removal of moisture, and removal of a solvent by vacuum distillation, the precipitated solid was washed with ethanol, and filtered so as to provide 219 g of Formula 1-a (79.8%).

2) Synthesis of a Compound Represented by Formula 1-b
According to Reaction Scheme 2 below, a compound represented by Formula 1-b was synthesized.

[Reaction Scheme 2]

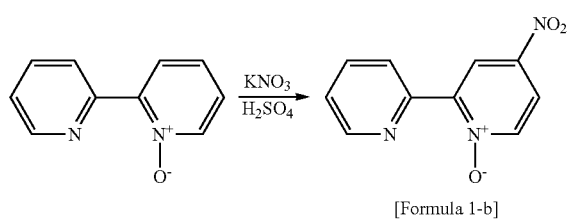

[Formula 1-b]

A 5 L round-bottom flask was charged with 219.2 g of Formula 1a (1.27 mol), and added with 1705 g of sulfuric acid, followed by stirring. 679.5 g of potassium nitride (7.98 mol) was slowly added thereto, followed by stirring at 90° C. for 23 hours. The temperature was lowered down to room temperature. Then, the resultant product was slowly poured to 2.0 L of cool water, and then neutralized with a potassium hydroxide aqueous solution, and extracted with methylene chloride. Then, an organic layer was separated. After removal of moisture, and removal of a solvent by vacuum distillation, 140 g of Formula 1-b (yield 50%) was obtained.

3) Synthesis of a Compound Represented by Formula 1-c
According to Reaction Scheme 3 below, a compound represented by Formula 1-c was synthesized.

[Reaction Scheme 3]

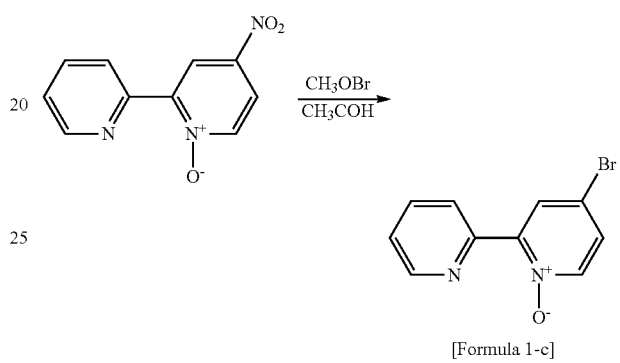

[Formula 1-c]

A 10 L round-bottom flask was charged with 140 g of Formula 1-b (0.65 mol), added with 1.4 L of acetic acid, and at 60° C., slowly dropwise added with 2.4 L of acetyl bromide (AcBr) (19.35 mol). The resultant product was stirred under reflux at 90° C. for 9 hours, cooled to room temperature, added to 2.7 L of cool water, added with a potassium hydroxide aqueous solution until pH reached 9 to 10, and extracted with methylene chloride. Then, an organic layer was separated. After removal of moisture, and removal of a solvent by vacuum distillation, 107 g of Formula 1-c (yield 66%) was obtained.

4) Synthesis of a Compound Represented by Formula 1-d
According to Reaction Scheme 4 below, a compound represented by Formula 1-d was synthesized.

[Reaction Scheme 4]

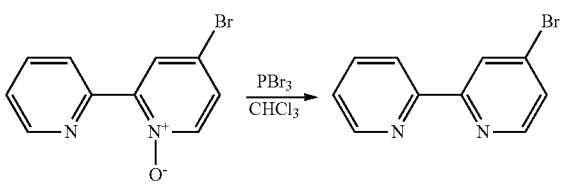

[Formula 1-d]

A 5 L round-bottom flask was substituted with nitrogen gas, and 107 g of Formula 1-c (0.43 mol) was added thereto, and dissolved by addition of 2.7 L of chloroform. At 0° C., 180.3 g of tribromophosphine (1.92 mol) was slowly dropwise added thereto, followed by stirring at 60° C. for 2 hours. The resultant product was cooled to room temperature, added to 2 L of water, added with a sodium hydroxide aqueous solution until pH reached 11, and extracted with methylene chloride. Then, an organic layer was separated. After removal of moisture, and removal of a solvent by vacuum distillation, the precipitated solid was washed with ethanol, and filtered so as to provide 100 g of Formula 1-d brown solid (yield 99%).

5) Synthesis of a Compound Represented by Formula 1-e
According to Reaction Scheme 5 below, a compound represented by Formula 1-e was synthesized.

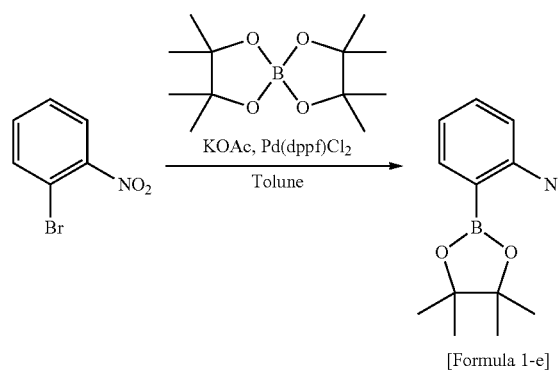

[Formula 1-e]

In a 2 L round-bottom flask, 100 g of bromonitrobenzene (0.50 mol) was charged, and dissolved by 1.5 L of toluene. The resultant solution was added with 150.9 g of bis(pinacolato)diboron (0.59 mol), 12.1 g of Pd(dppf)Cl$_2$ (0.015 mol), and 145.8 g of KOAc (1.49 mol), and refluxed for 10 hours. The solution was cooled to room temperature, and the solvent was removed by vacuum distillation. Then, the resultant solid was purified with column chromatography by using N-hexane as a developing solvent so as to provide 80 g of Formula 1-e (yield 65%).

6) Synthesis of a Compound Represented by Formula 1-f
According to Reaction Scheme 6 below, a compound represented by Formula 1-f was synthesized.

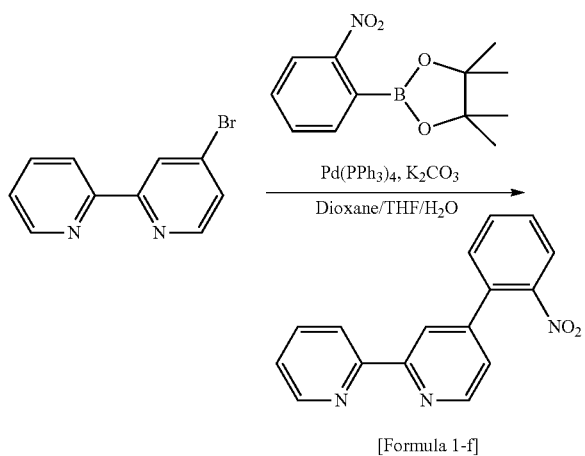

[Formula 1-f]

A 1 L round-bottom flask was charged with 100 g of Formula 1-d (0.43 mol), 148.2 g of Formula 1-e (0.60 mol), 117 g of potassium carbonate (K$_2$CO$_3$) (0.85 mol), 24.6 g of Pd(PPh$_3$)$_4$, 200 mL of water, 500 mL of dioxane and 100 mL of tetrahydrofuran, followed by reflux for 24 hours. After the reaction was completed, the resultant product was subjected to phase separation. The aqueous phase was removed, and the organic layer was separated, and vacuum-evaporated. Then, the resultant product was purified with column chromatography using hexane and ethylacetate as developing solvents so as to provide a solid. Finally, through drying, 65.7 g of a solid (yield 55%) was obtained.

7) Synthesis of Compounds Represented by Formulas 1-g and 1-h
According to Reaction Scheme 7 below, compounds represented by Formulas 1-g and 1-h were synthesized.

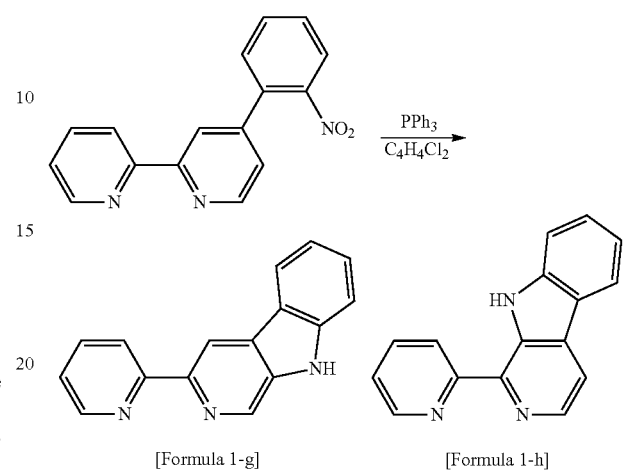

[Formula 1-g]                [Formula 1-h]

In a 1 L round-bottom flask, 65.7 g of Formula 1-f (0.24 mol), and 311.0 g of triphenylphosphine (1.19 mol), dissolved in 800 mL of o-dichlorobenzene, were refluxed for 24 hours. After the reaction was completed, the solution was cooled to room temperature, and the solvent was removed through vacuum distillation. Then, the resultant solid was purified with column chromatography using hexane and ethylacetate as developing solvents so as to provide a pale yellow solid, that is, 5.7 g of Formula 1-g (yield 9.8%), and 20.0 g of Formula 1-h (yield 34%).

8) Synthesis of a Compound Represented by Formula 1-i
According to Reaction Scheme 8 below, a compound represented by Formula 1-i was synthesized.

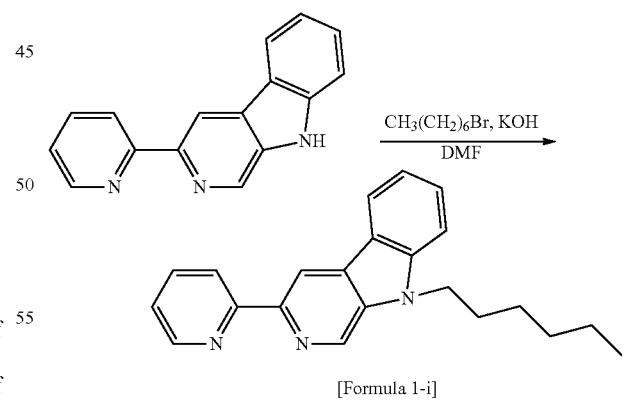

[Formula 1-i]

In 100 mL round-bottom flask, 2.0 g of Formula 1-g (0.01 mol), 10.0 g of 1-bromohexane (0.06 mol), and 2.3 g of potassium hydroxide (0.04 mol) were dissolved in 50 mL of N,N-dimethylformamide, followed by reflux for 12 hours. After the reaction was completed, the solution was cooled to room temperature, and extracted with ethyl acetate. The organic layer was separated. After removal of moisture, and removal of a solvent by vacuum distillation, the resultant product was purified with column chromatography by using hexane and ethylacetate as developing solvents so as to provide 1.7 g of Formula 1-i (yield 64.5%).

9) Synthesis of a Compound Represented by Formula 6

According to Reaction Scheme 9 below, a compound represented by Formula 6 was synthesized.

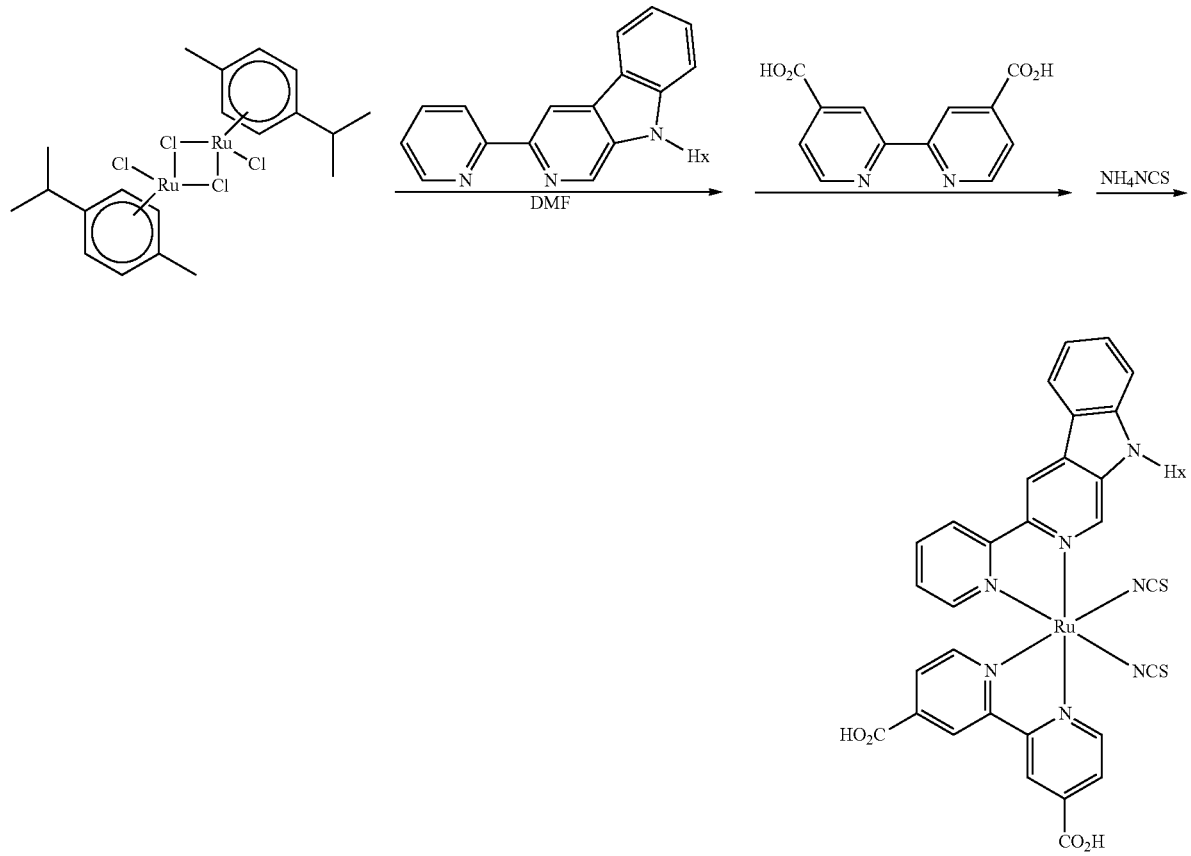

In a 500 mL round-bottom flask, 1.5 g of dichloro(p-cymene)ruthenium(II) dimer (0.0024 mol) was dissolved in 75 mL of N,N-dimethylformamide. Herein, light was blocked. The solution was added with 1.6 g of Formula 1-i (0.0045 mol), followed by stirring at 80° C. for 4 hours. The resultant solution was added with 1.7 g of 4,4'-dicarboxylic acid-2,2'-bipyridine (0.0048 mol), followed by stirring at 140° C. for 4 hours. The resultant solution was added with 11.0 g of NH$_4$NCS (0.144 mol), followed by stirring at 140° C. for 4 hours. The reaction solution was cooled to room temperature, and removed under reduced pressure. Then, a solid obtained by addition of excess water was filtered. The filtered solid was washed with excess water and ethanol, and purified with column chromatography by using water as a developing solvent, and sepadex as filler so as to provide 0.4 g of Formula 6 (yield 18.4%).

$^1$H NMR [DMSO, ppm]; 9.65 (s, 1H), 9.57 (s, 1H), 9.47 (d, 1H), 9.11 (s, 1H), 8.96 (s, 1H), 8.57 (d, 1H), 8.51 (d, 1H), 7.92 (t, 1H), 7.79 (t, 1H), 7.68 (d, 1H), 7.47 (dt, 2H), 7.45 (t, 1H), 1.34-1.23 (m, 5H), 0.93 (t, 6H), 0.76 (t, 3H).

Synthesis Example 2

Preparation of a Compound Represented by Formula 8

1) Synthesis of a Compound Represented by Formula 2-a

According to Reaction Scheme 1 below, a compound represented by Formula 2-a was synthesized.

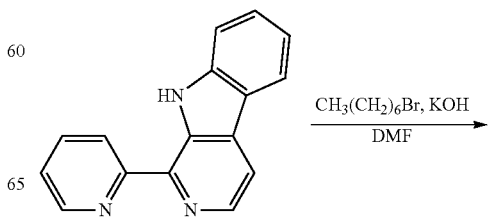

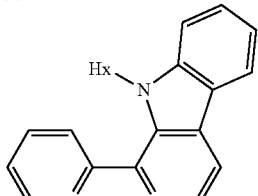

[Formula 2-a]

In a 100 mL round-bottom flask, 2.0 g of Formula 1-g (0.01 mol), 10.0 g of 1-bromohexane (0.06 mol), and 2.3 g of potassium hydroxide (0.04 mol) were dissolved in 50 mL of N,N-dimethylformamide and were refluxed for 12 hours. After the reaction was completed, the solution was cooled to room temperature, and extracted with ethyl acetate. The organic layer was separated. After removal of moisture, and removal of a solvent by vacuum distillation, the resultant product was purified with column chromatography by using hexane and ethylacetate as developing solvents so as to provide 1.7 g of Formula 2-a (yield 64.5%).

2) Synthesis of a Compound Represented by Formula 8

According to Reaction Scheme 2 below, a compound represented by Formula 8 was synthesized.

In a 500 mL round-bottom flask, 1.5 g of dichloro(p-cymene)ruthenium(II) dimer (0.0024 mol) was dissolved in 75 mL of N,N-dimethylformamide. Herein, light was blocked. The solution was added with 1.6 g of Formula 2-a (0.0045 mol), followed by stirring at 80° C. for 4 hours. The resultant solution was added with 1.7 g of 4,4'-dicarboxylic acid-2,2'-bipyridine (0.0048 mol), followed by stirring at 140° C. for 4 hours. The resultant solution was added with 11.0 g of NH$_4$NCS (0.144 mol), followed by stirring at 140° C. for 4 hours. The reaction solution was cooled to room temperature, and removed under reduced pressure. Then, a solid obtained by addition of excess water was filtered. The filtered solid was washed with excess water and ethanol, and purified with column chromatography by using water as a developing solvent, and sepadex as filler so as to provide 0.4 g of Formula 6 (yield 18.4%).

$^1$H NMR [DMSO, ppm]; 9.45 (d, 1H), 9.08 (d, 2H), 8.93 (s, 1H), 8.76 (d, 1H), 8.50 (d, 1H), 8.31 (dd, 1H), 8.17 (d, 1H), 8.02 (t, 2H), 7.75 (dd, 2H), 7.61-7.54 (m, 3H), 7.27 (t, 1H), 1.35-1.27 (m, 6H), 0.94 (t, 4H), 0.52 (t, 3H).

Synthesis Example 3

Preparation of a Compound Represented by Fomula 16

1) Synthesis of a Compound Represented by Formula 3-a

According to Reaction Scheme 1 below, a compound represented by Formula 3-a was synthesized.

[Reaction Scheme 2]

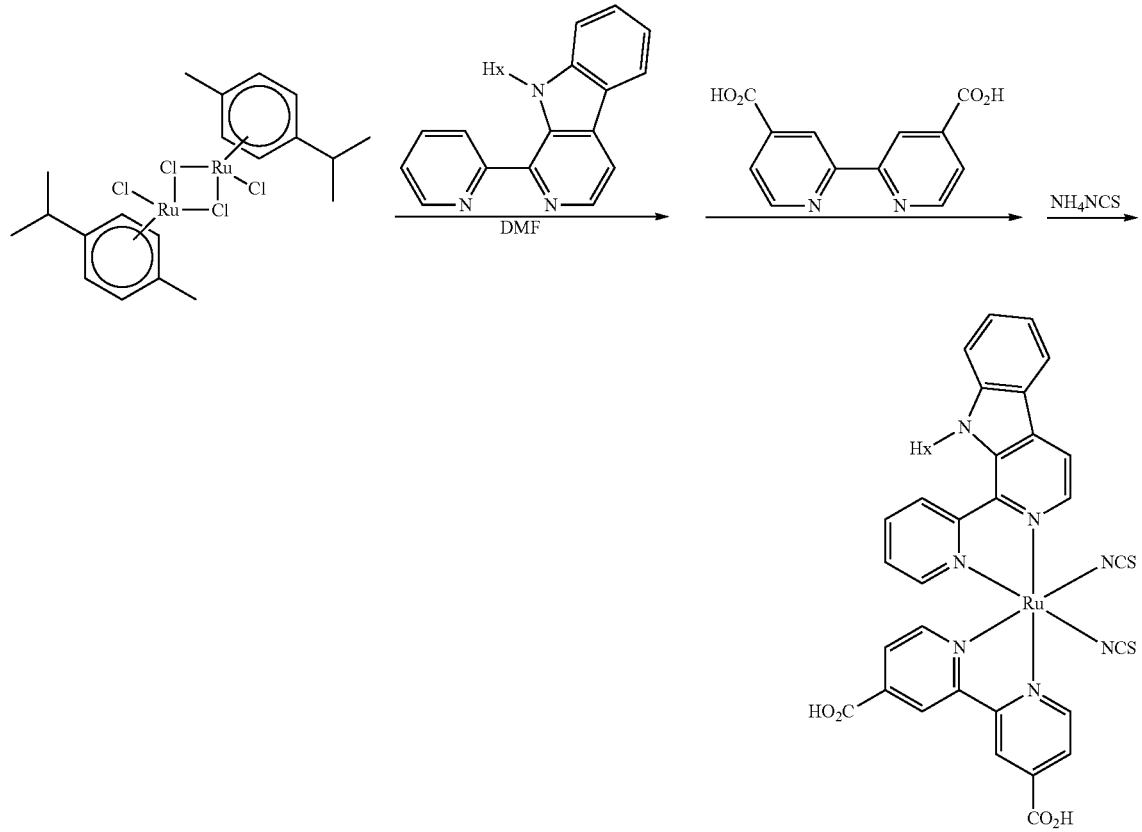

[Formula 8]

[Reaction Scheme 1]

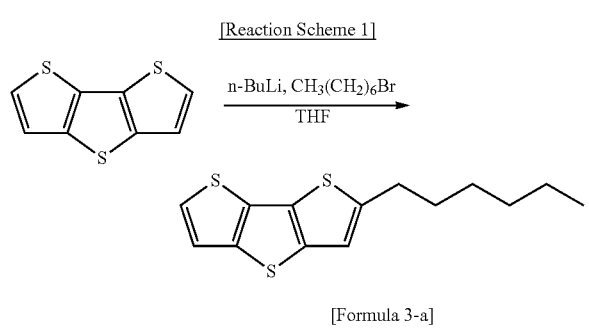

[Formula 3-a]

In a 1 L round-bottom flask, 116.6 g of dithienothiophene (0.594 mol) was dissolved in 500 mL of tetrahydrofuran (THF), followed by stirring at −78° C. for 30 minutes. 371 mL of n-butyllithium (1.6M hexane solution) (0.594 mol) was slowly dropwise added thereto, followed by stirring for 2 hours. The resultant solution was slowly added with 98 g of 1-bromohexane (0.594 mol), stirred at room temperature for 3 hours, and added with 200 mL of water. The organic layer was separated by ethyl acetate (AcEt), and the organic solvent was removed under reduced pressure so as to provide oil. The oil layer was vacuum-distillated so as to provide 96.6 g of Formula 3-a (yield 58%).

2) Synthesis of a Compound Represented by Formula 3-b

According to Reaction Scheme 2 below, a compound represented by Formula 3-b was synthesized.

[Reaction Scheme 2]

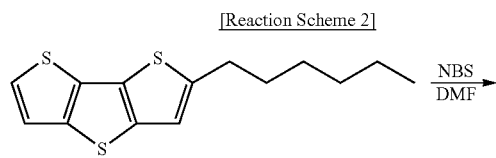

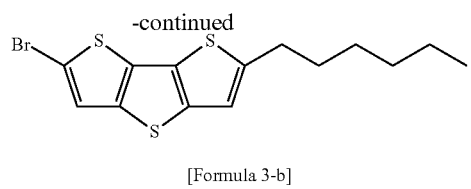

[Formula 3-b]

In a 5 L round-bottom flask, 90 g of Formula 3-a (0.321 mol) was dissolved in 1.8 L of N,N-dimethylformamide. The resultant solution was slowly added with 62.8 g of NBS (0.353 mol) at 0° C., and stirred at room temperature until a solid was precipitated. The resultant product was poured to 3.6 L of water, and the solid was filtered and purified with column chromatography using hexane as a developing solvent so as to provide 102.7 g of Formula 3-b (yield 89%).

3) Synthesis of a Compound Represented by Formula 3-c

According to Reaction Scheme 3 below, a compound represented by Formula 3-c was synthesized.

[Reaction Scheme 3]

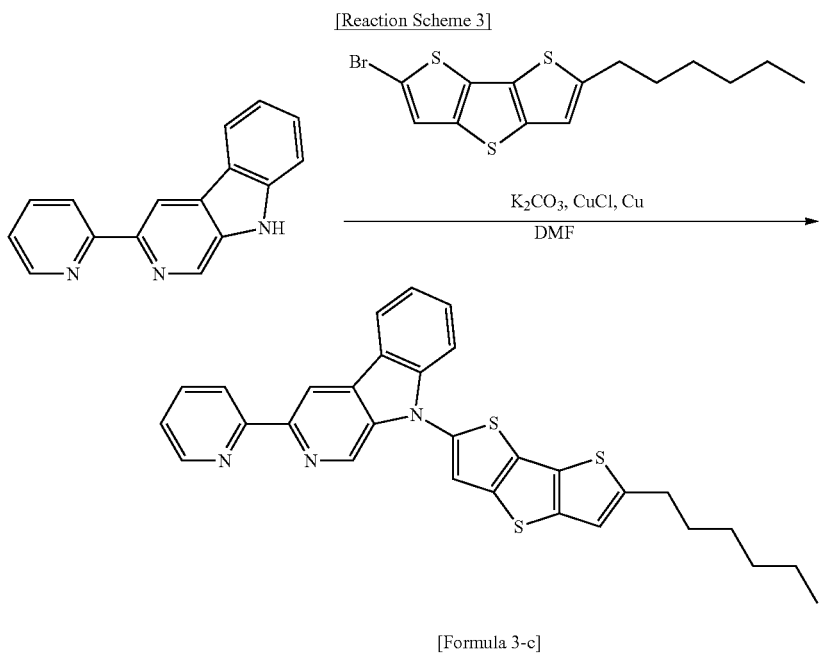

[Formula 3-c]

In a 100 mL round-bottom flask, 2.0 g of Formula 1-g (0.01 mol), Formula 3-b of 6.3 g (0.012 mol), 2.8 g of potassium carbonate (0.02 mol), 0.4 g of copper chloride (0.004 mol), and 0.25 g of copper (0.004 mol) were dissolved in 50 mL of N,N-dimethylformamide and were refluxed for 18 hours. After the reaction was completed, the solution was cooled to room temperature, and extracted with methylene chloride. The organic layer was separated. After removal of moisture, and removal of a solvent by vacuum distillation, the resultant product was purified with column chromatography by using hexane and ethyl acetate as developing solvents so as to provide 3.4 g of Formula 3-c (yield 64%).

4) Synthesis of a Compound Represented by Formula 16

According to Reaction Scheme 4 below, a compound represented by Formula 16 was synthesized.

[Reaction Scheme 4]

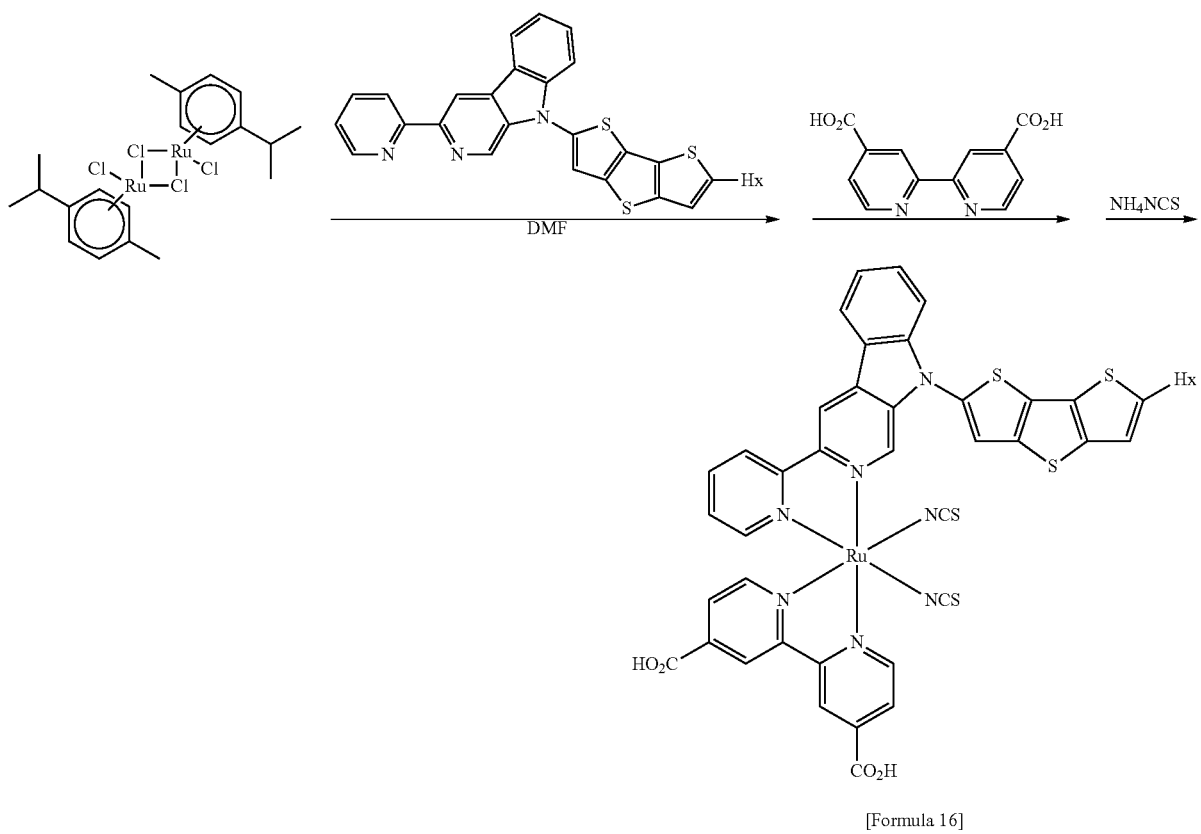

[Formula 16]

In a 500 mL round-bottom flask, 1.5 g of dichloro(p-cymene)ruthenium(II) dimer (0.0024 mol) was dissolved in 75 mL of N,N-dimethylformamide. Herein, light was blocked. The solution was added with 2.4 g of Formula 3-c (0.0045 mol), followed by stirring at 80° C. for 4 hours. The resultant solution was added with 1.7 g of 4,4'-dicarboxylic acid-2,2'-bipyridine (0.0048 mol), followed by stirring at 140° C. for 4 hours. The resultant solution was added with 11.0 g of NH$_4$NCS (0.144 mol), followed by stirring at 140° C. for 4 hours. The reaction solution was cooled to room temperature, and removed under reduced pressure. Then, a solid obtained by addition of excess water was filtered. The filtered solid was washed with excess water and ethanol, and purified with column chromatography by using water as a developing solvent, and sepadex as filler so as to provide 0.7 g of Formula 6 (yield 31.1%).

$^1$H NMR [DMSO, ppm]; 9.66 (s, 1H), 9.58 (s, 1H), 9.50 (d, 1H), 9.11 (d, 2H), 8.68 (d, 1H), 8.43 (d, 2H), 8.38 (d, 1H), 7.95 (t, 2H), 7.82 (t, 1H), 7.49 (dd, 3H), 7.45 (t, 1H), 7.38 (d, 1H), 7.30 (d, 1H), 2.83 (t, 2H), 1.76-1.72 (m, 2H), 1.35 (t, 6H), 0.92 (t, 3H).

Synthesis Example 4

Preparation of a Compound Represented by Formula 48

1) Synthesis of a Compound Represented by Formula 4-a

According to Reaction Scheme 1 below, a compound represented by Formula 4-a was synthesized.

[Reaction Scheme 1]

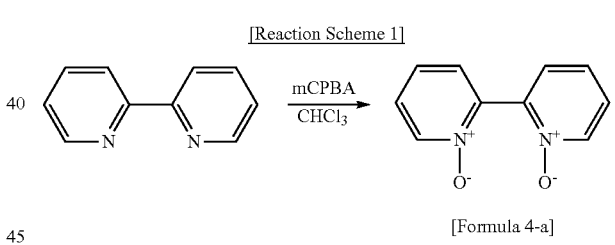

[Formula 4-a]

In a 5 L round-bottom flask, 165 g of 2,2'-bipyridine (1.05 mol) was dissolved in 570 mL of chloroform, and cooled down to −78° C. 389 g of m-chloroper benzoic acid (2.25 mol) dissolved in 1,520 mL of chloroform was added thereto. At room temperature, the resultant product was stirred for 12 hours, and the resultant solid was filtered. The solid was washed with methanol, and filtered. This step was repeated twice so as to provide a white solid, 172.3 g of Formula 4-a (yield 89.4%).

2) Synthesis of a Compound Represented by Formula 4-b

According to Reaction Scheme 2 below, a compound represented by Formula 4-b was synthesized.

[Reaction Scheme 2]

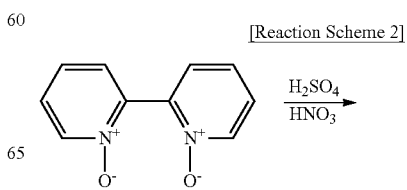

-continued

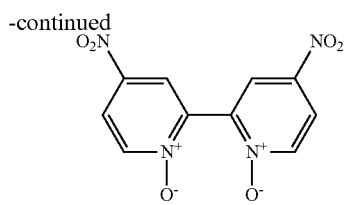

[Formula 4-b]

A 2 L round-bottom flask was charged with 199 g of an intermediate 28a (1.06 mol), and with 1038 g of oleum sulfuric acid (10.58 mol), followed by stirring. Fuming nitric acid was slowly dropwise added thereto, at low temperature, followed by stirring at 80° C. for 12 hours. The temperature was lowered to room temperature, and the resultant product was slowly poured to 4.5 L of cool water. The resultant solid was filtered, and sufficiently washed with water so as to provide a yellow solid, 126.9 g of Formula 4-b (yield 43%).

3) Synthesis of a Compound Represented by Formula 4-c

According to Reaction Scheme 3 below, a compound represented by Formula 4-c was synthesized.

[Reaction Scheme 3]

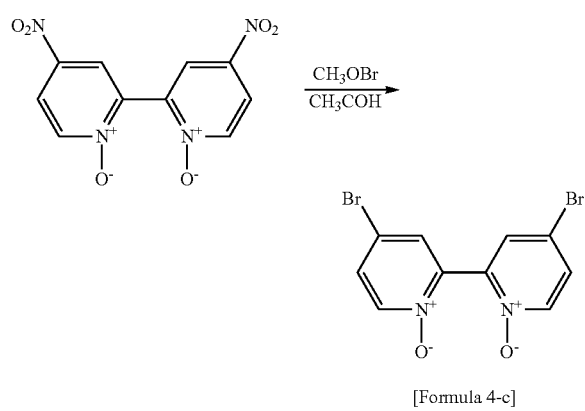

[Formula 4-c]

A 5 L round-bottom flask was charged with 126 g of intermediate 28c (0.456 mol), and with 1.9 L of acetic acid. Then, at 40° C., 140 g of acetyl bromide (1.14 mol) was slowly added thereto. After 3 hours, the resultant product was cooled down to room temperature, and then poured to 19 L of cool water, and then neutralized with sodium hydroxide. The resultant solid was washed with methanol, and filtered. This step was repeated twice so as to provide a pale yellow solid, 116 g of Formula 4-c (yield 74%).

4) Synthesis of a Compound Represented by Formula 4-d

According to Reaction Scheme 4 below, a compound represented by Formula 4-d was synthesized.

[Reaction Scheme 4]

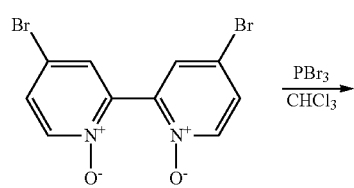

-continued

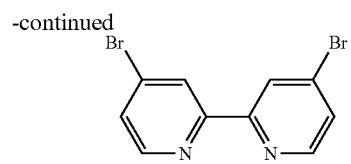

[Formula 4-d]

A 2 L round-bottom flask was substituted with nitrogen gas, and 37 g of Formula 4-c (0.1 mol) was added thereto, and dissolved by addition of 950 mL of chloroform. At −3° C., 297 g of tribromophosphine (1.1 mol) was slowly dropwise added thereto, followed by stirring at 60° C., for 2 hours. The resultant product was cooled to room temperature, added to 1 L of water, added with caustic soda until pH reached 11, and extracted with methylene chloride. Then, an organic layer was separated. After removal of moisture, and removal of a solvent by vacuum distillation, the precipitated solid was washed with ethanol, and filtered so as to provide a pale yellow solid, 26 g of Formula 4-d (yield 77%).

5) Synthesis of a Compound Represented by Formula 4-e

According to Reaction Scheme 5 below, a compound represented by Formula 4-e was synthesized.

[Reaction Scheme 5]

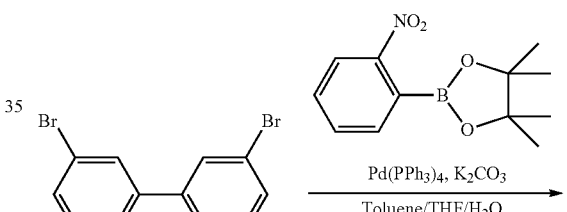

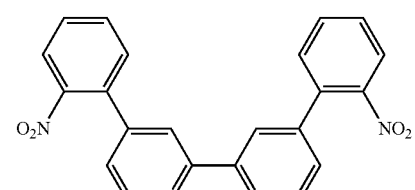

[Formula 4-e]

A 500 ml round-bottom flask was charged with 25 g of Formula 4-d (0.080 mol), 47.6 g of Formula 1-e (0.191 mol), 22.1 g of potassium carbonate ($K_2CO_3$) (0.160 mol), 4.6 g of Pd(PPh$_3$)$_4$, 40 mL of water, 100 ml of toluene, and 100 mL of tetrahydrofuran, followed by reflux for 24 hours. After the reaction was completed, the resultant product was subjected to phase separation. The aqueous phase was removed, and the organic layer was separated, and vacuum-evaporated. Then, the resultant product was purified with column chromatography using hexane and dichloromethane as developing solvents so as to provide a solid. Finally, through drying, a white solid, 12.7 g of Formula 4-e (yield 87%) was obtained.

6) Synthesis of a Compound Represented by Formula 4-f

According to Reaction Scheme 6 below, compounds represented by Formulas 4-f and 4-g were synthesized.

[Reaction Scheme 6]

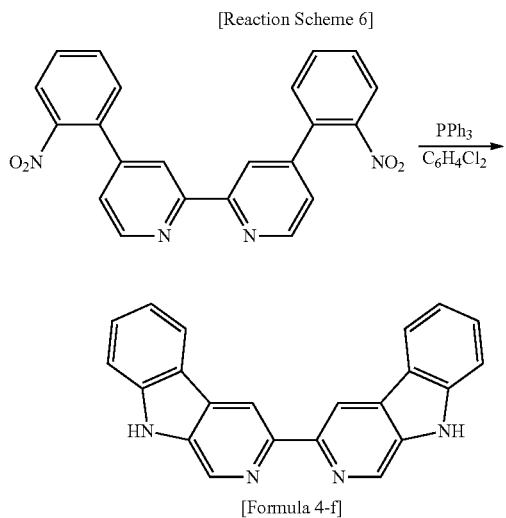

[Formula 4-f]

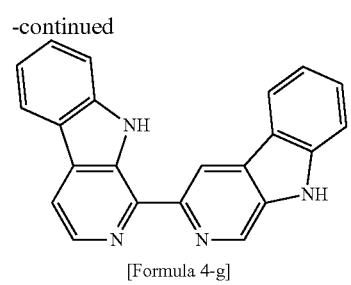

[Formula 4-g]

In a 500 ml round-bottom flask, 13.0 g of Formula 4-e (0.033 mol), and 42.7 g of triphenylphosphine (0.163 mol) were dissolved in 200 mL of o-dichlorobenzene, and refluxed for 24 hours. After the reaction was completed, the solution was cooled to room temperature, and the solvent was removed through vacuum distillation. Then, the resultant solid was purified with column chromatography using dichloromethane as a developing solvent so as to provide a pale yellow solid, that is, 5.9 g of Formula 4-f (yield 54%), and 2.4 g of Formula 4-g (yield 22%).

7) Synthesis of a Compound Represented by Formula 48

According to Reaction Scheme 7 below, a compound represented by Formula 48 was synthesized.

[Reaction Scheme 7]

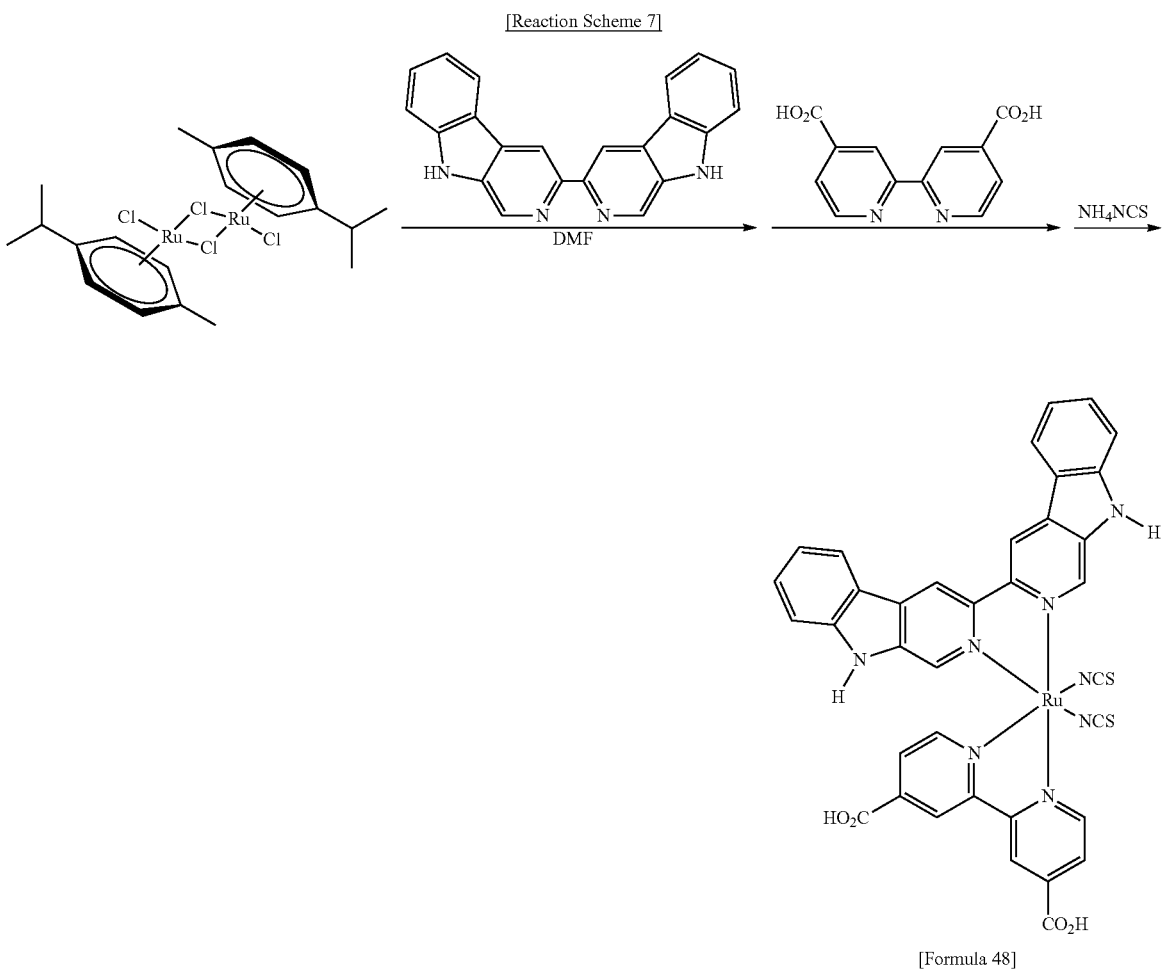

[Formula 48]

In a 250 mL round-bottom flask, 5.2 g of dichloro(p-cymene)ruthenium(II) dimer (0.0085 mol) was dissolved in 100 mL of DMF. Herein, light was blocked. The solution was added with 5.7 g of Formula 4-f (0.017 mol), followed by stirring at 80° C. for 4 hours. The resultant solution was added with 4.15 g of 4,4'-dicarboxylic acid-2,2'-bipyridine (0.017 mol), followed by stirring at 140° C. for 4 hours. The resultant solution was added with 53.52 g of NH$_4$NCS (0.703 mol), followed by stirring at 140° C. for 4 hours. The reaction solution was cooled to room temperature, and removed under reduced pressure. Then, a solid obtained by addition of excess water was filtered. The filtered solid was washed with excess water and ethanol, and purified with column chromatography by using water as a developing solvent, and sepadex as filler so as to provide 2.36 g of Formula 48 (yield 35%).

$^1$H NMR [DMSO, ppm]; 10.41 (s, 2H), 9.43 (s, 1H), 9.36 (s, 1H), 9.25 (s, 1H), 9.19 (s, 1H), 9.11 (d, 1H), 9.06 (d, 1H), 8.87 (s, 1H), 8.77 (s, 1H), 8.59 (s, 1H), 8.45 (s, 1H), 7.63 (d, 2H), 7.58 (t, 2H), 7.38 (dd, 2H), 7.29 (dt, 2H).

Synthesis Example 5

Preparation of a Compound Represented by Formula 55

1) Synthesis of a Compound Represented by Formula 5-a

According to Reaction Scheme 1 below, a compound represented by Formula 5-a was synthesized.

[Reaction Scheme 1]

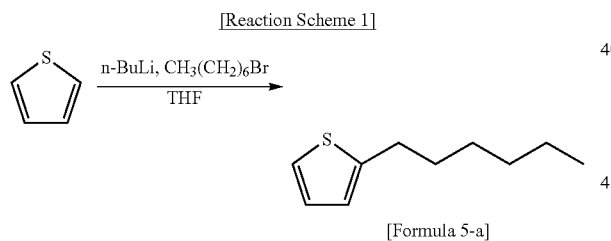

[Formula 5-a]

In a 1 L round-bottom flask, 50 g of thiophene (0.594 mol) was dissolved in 500 mL of tetrahydrofuran (THF), followed by stirring at −78° C. for 30 minutes. 371 mL of n-butyllithium (1.6M hexane solution) (0.594 mol) was slowly dropwise added thereto, followed by stirring for 2 hours. The resultant solution was slowly added with 98 g of 1-bromohexane (0.594 mol), stirred at room temperature for 3 hours, and added with 200 mL of water. The organic layer was separated by ethyl acetate (AcEt), and the organic solvent was removed under reduced pressure so as to provide oil. The oil layer was vacuum-distillated so as to provide 52.2 g of Formula 5-a (yield 52%).

2) Synthesis of a Compound Represented by Formula 5-b

According to Reaction Scheme 2 below, a compound represented by Formula 5-b was synthesized.

[Reaction Scheme 2]

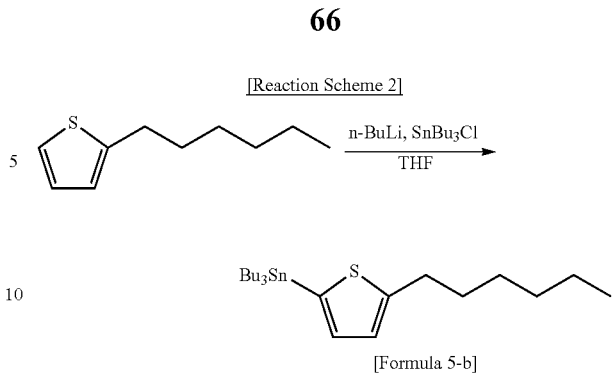

[Formula 5-b]

In a 1 L round-bottom flask, 52.2 g of Formula 5-a (0.310 mol) was dissolved in 500 mL of tetrahydrofuran (THF), followed by stirring at −78° C. for 30 minutes. 233 mL of n-butyllithium (1.6M hexane solution) (0.372 mol) was slowly dropwise added thereto, followed by stirring for 2 hours. The resultant solution was slowly added with 131 g of SnBu$_3$Cl (0.403 mol), stirred at room temperature for 3 hours, and added with 200 mL of water. The organic layer was separated by ethyl acetate (AcEt), and the organic solvent was removed under reduced pressure so as to provide oil. The oil layer was vacuum distillated so as to provide 101 g of Formula 5-b (yield 71%).

3) Synthesis of a Compound Represented by Formula 5-c

According to Reaction Scheme 3 below, a compound represented by Formula 5-c was synthesized.

[Reaction Scheme 3]

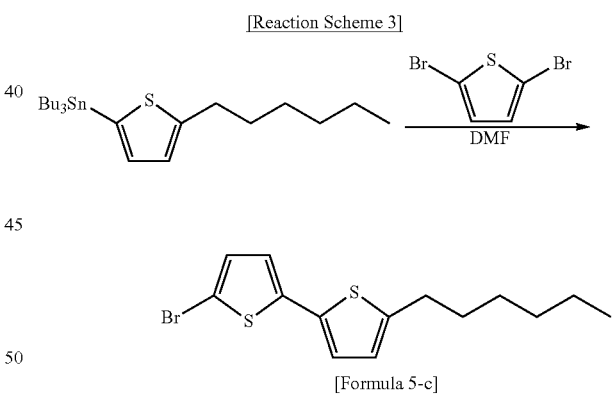

[Formula 5-c]

In a 1 L round-bottom flask, 137 g of Formula 5-b (0.30 mol) and 108.5 g of 2,5-dibromothiophene (0.45 mol) were dissolved in 400 mL of DMF, followed by stirring at 85° C. for 12 hours. The solution was pressure-reduced so as to remove the solvent. Then, the remaining oil was purified with column chromatography using hexane as a developing solvent so as to provide 74 g of Formula 5-c (yield 75%).

4) Synthesis of a Compound Represented by Formula 5-d

According to Reaction Scheme 4 below, a compound represented by Formula 5-d was synthesized.

[Reaction Scheme 4]

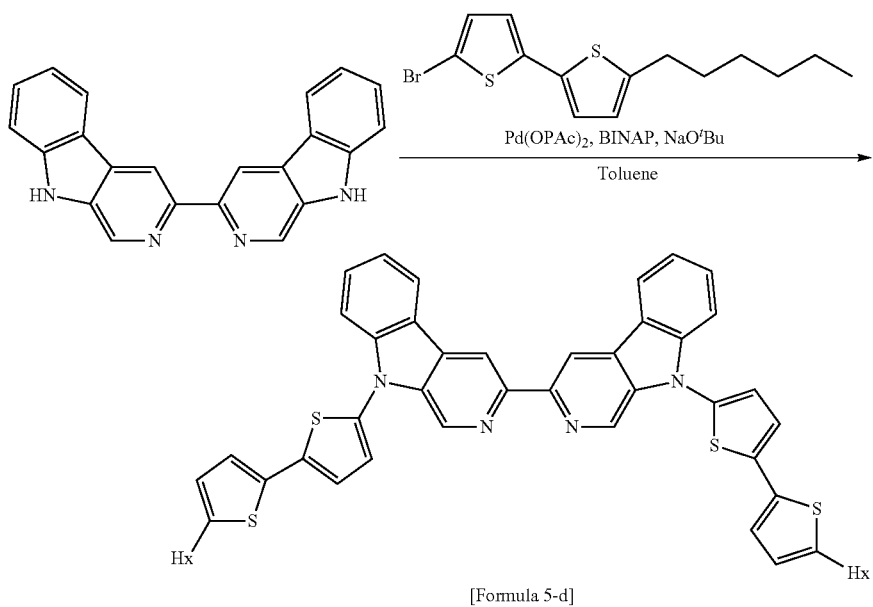

[Formula 5-d]

A 250 mL round-bottom flask was charged with Formula 4-f 28 g 10.0 g (0.030 mol), 28 g of Formula 5-c 21.7 g (0.066 mol), 0.74 g of BINAP, 7.19 g of NaO$^t$Bu (0.07 mol), 0.27 g of palladium acetate (Pd(OAc)$_2$), and 100 ml of toluene, followed by reflux for 24 hours. After the reaction was completed, the organic solvent was subjected to vacuum distillation. Through extraction with ethyl acetate and water, the organic layer was separated. The solvent was removed, and the obtained solid was washed with methanol, and purified with column chromatography using hexane and dichloromethane (1:1) as developing solvents. Finally, through drying, a solid, 21.4 g of Formula 5-d (yield 72%) was obtained.

5) Synthesis of a Compound Represented by Formula 55

According to Reaction Scheme 5 below, a compound represented by Formula 55 was synthesized.

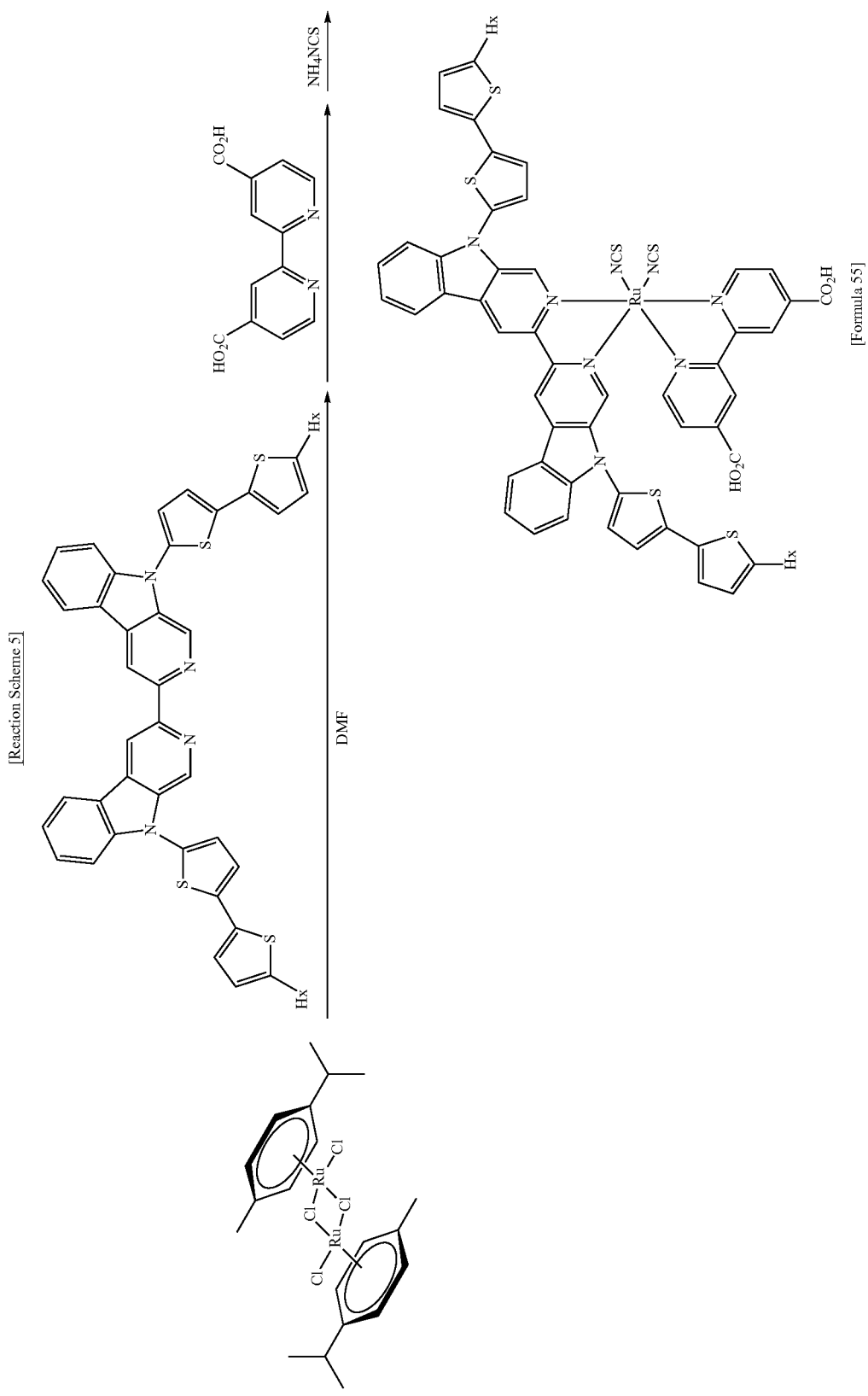

2.5 g of Formula 55, (yield 26%) was obtained in the same manner as described in Synthesis Example of Formula 48 except that instead of Formula 4-f, Formula 5-d was used.

$^1$H NMR [DMSO, ppm]; 9.56 (d, 1H), 9.19 (dt, 1H), 9.13 (d, 2H), 8.97 (s, 1H), 8.66 (d, 1H), 8.55 (s, 1H), 8.43 (t, 2H), 8.13 (d, 2H), 7.71-7.69 (m, 2H), 7.51 (d, 1H), 7.39 (d, 2H), 7.23-7.19 (m, 3H), 7.15 (d, 1H), 6.89 (s, 1H), 1.31-1.24 (m, 10H), 0.94 (t, 12H), 0.75 (t, 6H).

Synthesis Example 6

Preparation of a Compound Represented by Formula 61

1) Synthesis of a Compound Represented by Formula 6-a

According to Reaction Scheme 1 below, a compound represented by Formula 6-a was synthesized.

[Reaction Scheme 1]

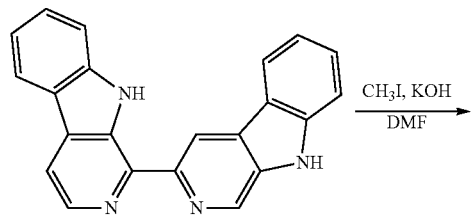

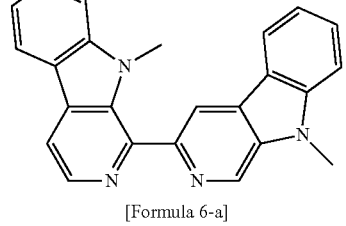

[Formula 6-a]

A 100 mL round-bottom flask was charged with 2.0 g of Formula 4-g (0.01 mol), 8.5 g of methyl iodide (0.06 mol), and 2.2 g of potassium hydroxide (0.04 mol), and added with 50 mL of N,N-dimethylformamide, followed by reflux for 12 hours. After the reaction was completed, the solution was cooled to room temperature, and extracted with ethyl acetate. The organic layer was separated. After removal of moisture, and removal of a solvent by vacuum distillation, the resultant product was purified with column chromatography by using hexane and ethylacetate as developing solvents so as to provide 2.7 g of Formula 6-a, (yield 75.1%).

2) Synthesis of a Compound Represented by Formula 61

According to Reaction Scheme 2 below, a compound represented by Formula 61 was synthesized.

[Reaction Scheme 2]

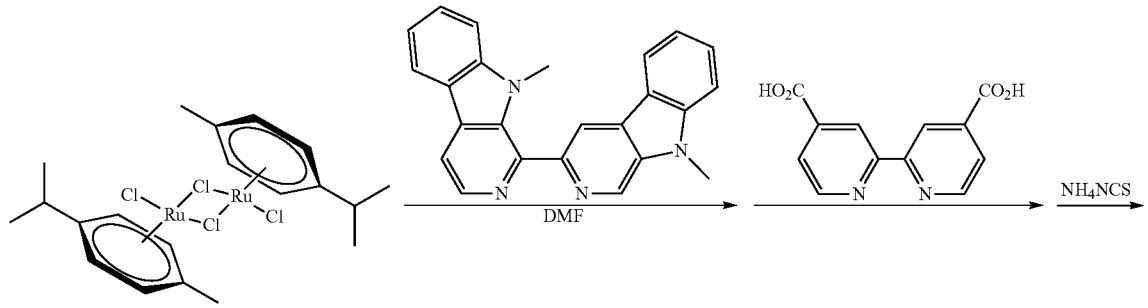

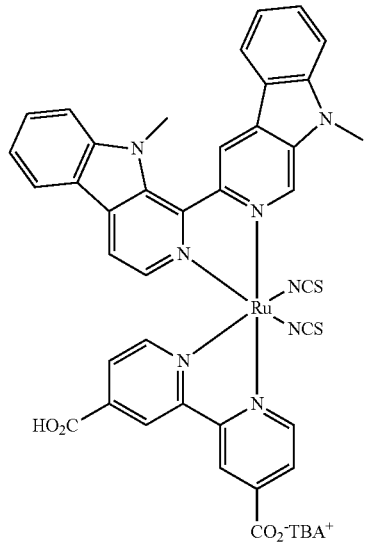

[Formula 61]

In a 250 mL round-bottom flask, 2.5 g of dichloro(p-cymene)ruthenium(II) dimer (0.0037 mol) was dissolved in 70 mL of DMF. Herein, light was blocked. The solution was added with 2.7 g of Formula 6-a (0.0074 mol), followed by stirring at 80° C. for 4 hours. The resultant solution was added with 2.6 g of 4,4'-dicarboxylic acid-2,2'-bipyridine (0.0074 mol), followed by stirring at 140° C. for 4 hours. The resultant solution was added with 22.53 g of NH$_4$NCS (0.296 mol), followed by stirring at 140° C. for 4 hours. The reaction solution was cooled to room temperature, and removed under reduced pressure. Then, a solid obtained by addition of excess water was filtered. The filtered solid was washed with excess water and ethanol, and purified with column chromatography by using water as a developing solvent, and sepadex as filler so as to provide 0.9 g of Formula 61 (yield 31%).

$^1$H NMR [DMSO, ppm]; 9.62 (s, 1H), 9.52 (d, 1H), 9.20 (s, 1H), 9.04 (m, 3H), 8.77 (d, 1H), 8.64 (d, 1H), 8.32 (d, 1H), 8.23 (d, 1H), 8.05 (d, 1H), 7.75 (m, 6H), 7.26 (d, 1H), 4.19 (s, 3H), 4.01 (s, 3H), 3.16 (m, 8H), 1.55 (m, 8H), 1.29 (m, 8H), 0.93 (t, 12H).

Synthesis Example 7

Preparation of a Compound Represented by Formula 64

1) Synthesis of a Compound Represented by Formula 7-a
According to Reaction Scheme 1 below, a compound represented by Formula 7-a was synthesized.

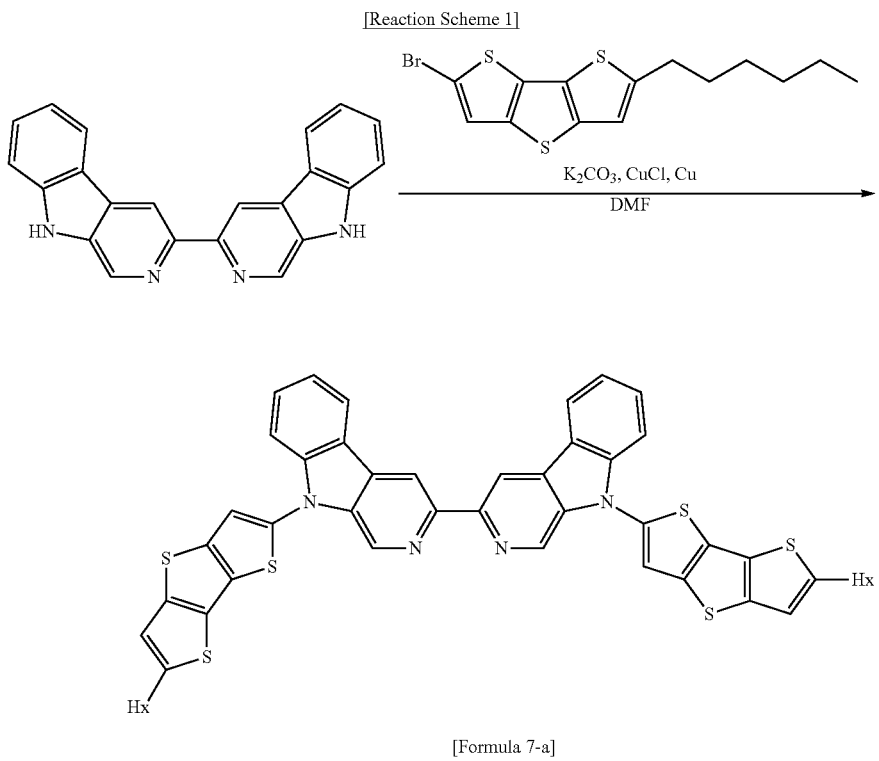

[Reaction Scheme 1]

[Formula 7-a]

In a 100 mL round-bottom flask, 2.0 g of Formula 4-f (0.006 mol), 6.4 g of Formula 3-b (0.018 mol), 3.3 g of potassium carbonate (0.024 mol), 0.2 g of copper chloride (0.0024 mol), and 0.15 g of copper (0.0024 mol) were dissolved in N,N-dimethylformamide 20 mL and were refluxed for 18 hours. After the reaction was completed, the solution was cooled to room temperature, and extracted with methylene chloride. The organic layer was separated. After removal of moisture, and removal of a solvent by vacuum distillation, the resultant product was purified with column chromatography by using hexane and ethyl acetate as developing solvents so as to provide 3.0 g of Formula 7-a (yield 71%).

2) Synthesis of a Compound Represented by Formula 64
According to Reaction Scheme 2 below, a compound represented by Formula 64 was synthesized.

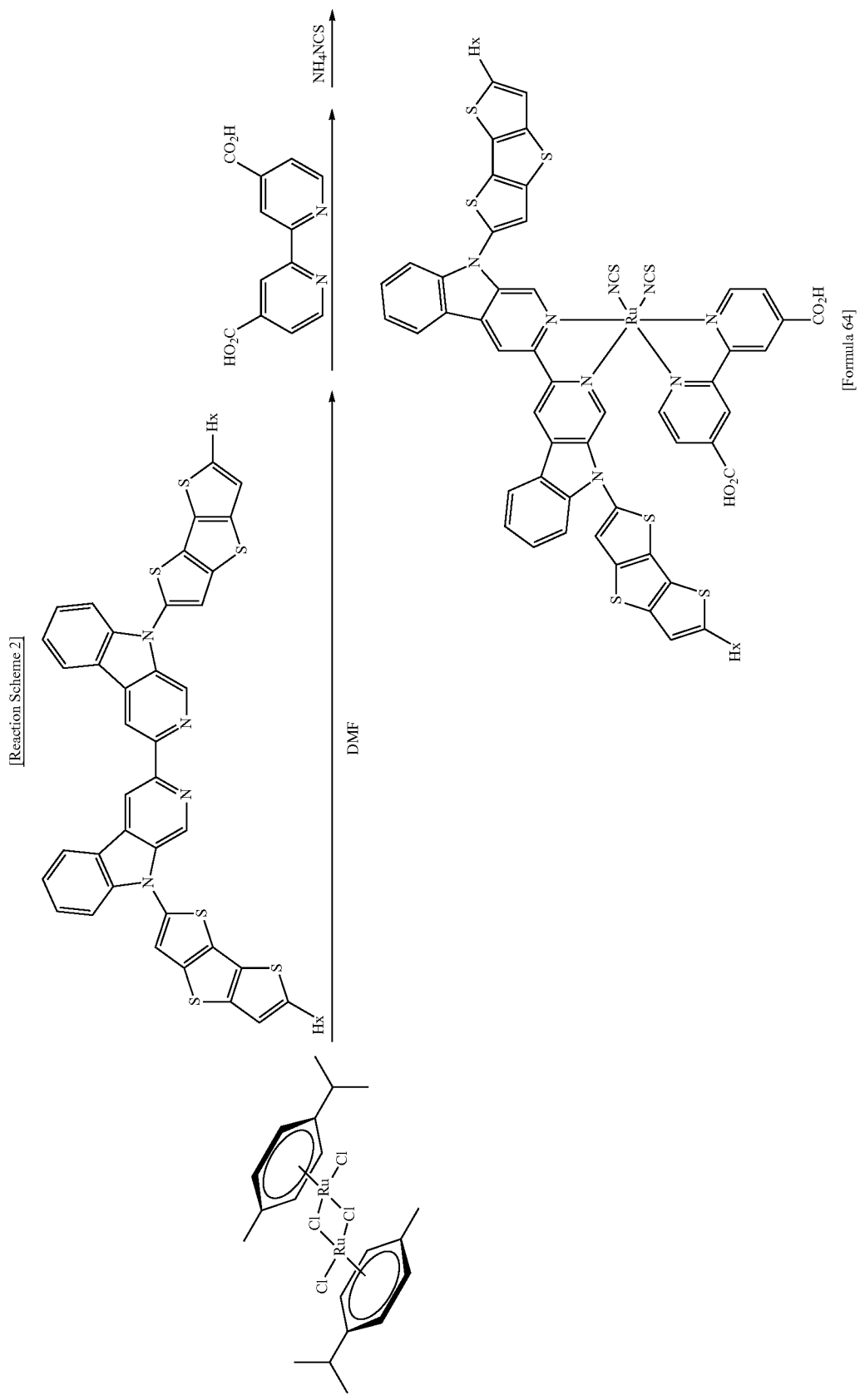

0.5 g of Formula 64, (yield 22%) was obtained in the same manner as described in Synthesis Example of Formula 48 except that instead of Formula 4-f, Formula 7-a was used.

$^1$H NMR [DMSO, ppm]; 9.68 (s, 2H), 9.59 (s, 2H), 9.51 (d, 2H), 9.14 (s, 2H), 9.09 (s, 2H), 8.63 (d, 2H), 8.57 (d, 2H), 8.33 (d, 2H), 8.04 (t, 4H), 7.96 (t, 2H), 7.74 (d, 2H), 7.65-7.58 (m, 6H), 7.51 (t, 2H), 7.39 (d, 2H), 7.33 (d, 2H), 2.84 (t, 4H), 1.75-1.72 (m, 4H), 1.33 (t, 12H), 0.94 (t, 6H).

Synthesis Example 8

Preparation of a Compound Represented by Formula 74

1) Synthesis of a Compound Represented by Formula 8-a

According to Reaction Scheme 1 below, a compound represented by Formula 8-a was synthesized.

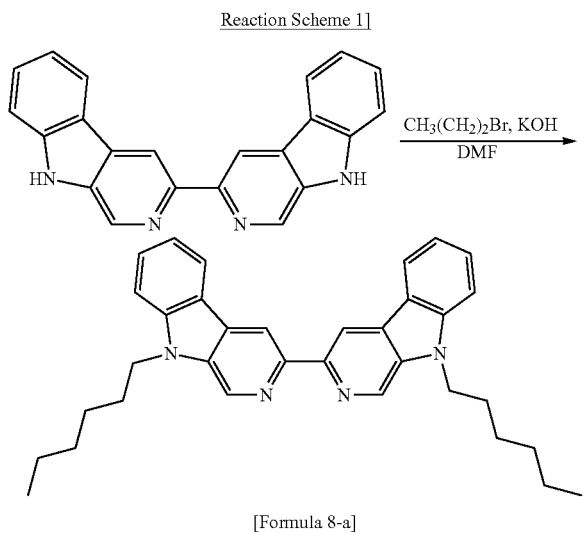

[Reaction Scheme 1]

[Formula 8-a]

In a 250 mL round-bottom flask, 10.0 g of Formula 4-f (0.030 mol) was dissolved in 100 mL of N,N-dimethylformamide. The solution was added with 12.3 g of 1-bromohexane (0.075 mol) and 12.4 g of potassium carbonate (0.09 mol), followed by reflux for 6 hours. The reaction solution was cooled to room temperature, and a solid obtained by addition of excess water was filtered. The filtered solid was purified with column chromatography by using hexane/ethylacetate (1:1) as a developing solvent so as to provide 8.3 g of Formula 8-a (yield 83%).

2) Synthesis of a Compound Represented by Formula 8-b

According to Reaction Scheme 2 below, a compound represented by Formula 8-b was synthesized.

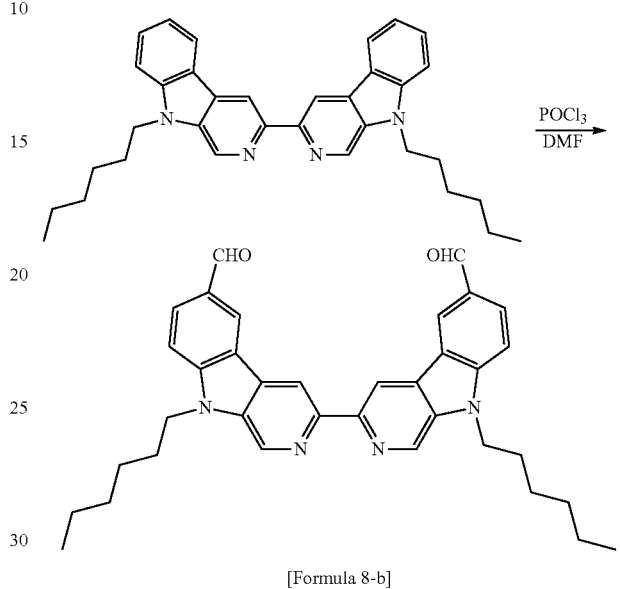

[Reaction Scheme 2]

[Formula 8-b]

In a 250 mL round-bottom flask, 15.0 g of Formula 8-a (0.045 mol) was dissolved in 100 mL of N,N-dimethylformamide. The solution was cooled to 0° C., added with 20.7 g of POCl$_3$ (0.135 mol), and stirred at room temperature for 1 hour. The solution was heated up to 90° C., and stirred for 10 hours. The solution was cooled to room temperature, and basified with addition of a potassium carbonate aqueous solution. Then, a solid obtained by addition of excess water was filtered. The filtered solid was purified with column chromatography by using hexane/ethylacetate (1:1) as a developing solvent so as to provide 9.9 g of Formula 8-b (yield 57%).

3) Synthesis of a Compound Represented by Formula 8-c

According to Reaction Scheme 3 below, a compound represented by Formula 8-c was synthesized.

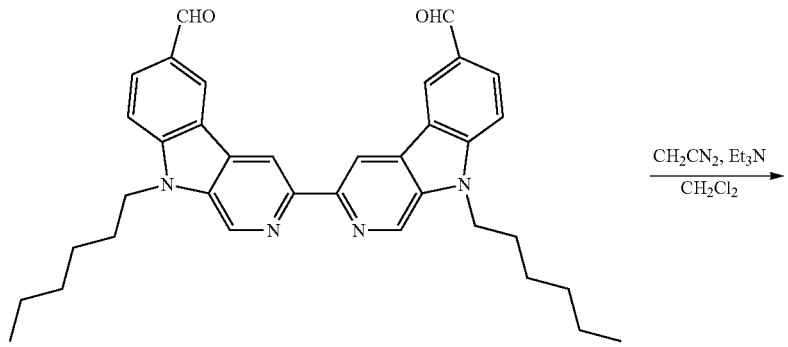

[Reaction Scheme 3]

[Formula 8-c]

In a 250 mL round-bottom flask, 5.0 g of Formula 8-b (0.013 mol) was dissolved in 100 mL of methylene chloride. The resultant solution was added with 2.8 g of malononitrile ($CH_2CN_2$) (0.052 mol), and 3-4 drops of triethylamine were added thereto. The solution was stirred for 3 hours, and the organic solvent was removed by vacuum distillation. Then, the resultant product was purified with column chromatography using hexane/ethylacetate (1:1) as a developing solvent so as to a yellow solid, 5.4 g of Formula 8-c (yield 85%).

4) Synthesis of a Compound Represented by Formula 74

According to Reaction Scheme 4 below, a compound represented by Formula 74 was synthesized.

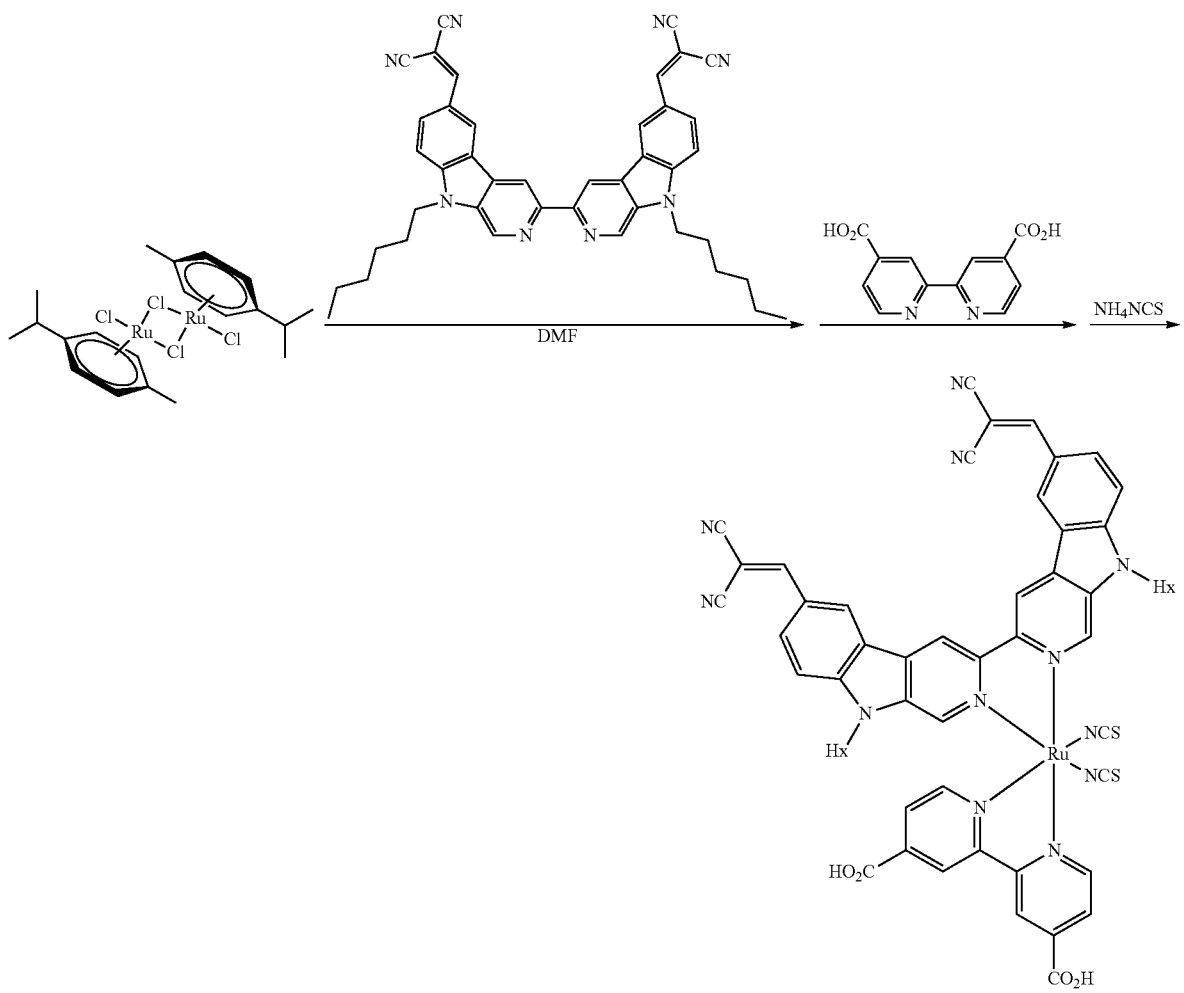

[Reaction Scheme 4]

[Formula 74]

3.7 g of Formula 74 (yield 29%) was obtained in the same manner as described in Synthesis Example of Formula 48 except that instead of Formula 4-f, Formula 8-c was used.

$^1$H NMR [DMSO, ppm]; 9.41 (s, 2H), 9.27 (d, 2H), 8.91 (s, 2H), 8.86 (s, 2H), 8.34 (s, 2H), 8.11 (s, 2H), 7.89 (d, 2H), 7.41 (d, 2H), 7.38 (d, 2H), 1.34-1.27 (m, 8H), 0.94 (t, 12H), 0.76 (t, 6H).

Examples 1 to 8

On an indium-doped tin oxide transparent conductor, titanium oxide dispersion with a particle diameter of 5 to 15 nm was coated on an area of 1 cm² by a doctor blade method, and subjected to heat treatment (firing) at 450° C. for 30 minutes so as to fabricate a porous titanium oxide thick film with a thickness of 18 μm. Then, a test piece was maintained at 80° C., and then was immersed in 0.3 mM dye dispersion having the above mentioned compounds represented by Formula 6, 8, 16, 48, 55, 61, 64, and 74 dissolved in ethanol, followed by dye-adsorbing treatment for 12 hours or more. Then, the dye-adsorbed porous titanium oxide thick film was washed with ethanol, and dried at room temperature. Then, a first electrode formed with a light absorbing layer was fabricated.

In fabrication of a second electrode, on an indium-doped tin oxide transparent conductor, a Pt layer was deposited by sputter to a thickness of about 200 nm. For injection of an electrolyte, a drill with a diameter of 0.75 mm was used to make a fine hole. Then, the second electrode was fabricated.

A thermoplastic polymer film with a thickness of 60 μm was compressed between the first electrode and the second electrode at 100° C. for 9 seconds so as to conjugate the two electrodes to each other. Through the fine hole formed in the second electrode, a redox electrolyte was injected, and then by using a cover glass and a thermoplastic polymer film, the fine hole was sealed. Then, a dye-sensitized solar cell was fabricated. Herein, the redox electrolyte was obtained by dissolving 0.62M 1,2-dimethyl-3-hexylimidazolium iodide, 0.5M 2-aminopyrimidine, 0.1M LiI and 0.05M I2 in an acetonitrile solvent.

Comparative Example

In Comparative Example, a dye-sensitized solar cell was fabricated in the same manner as described in Examples 1 to 8 except that instead of the organic metal dye, conventionally well known N719 (Formula 88) was used.

Herein, N719 is a ruthenium-based dye that has been conventionally used in a dye-sensitized solar cell, and its synthesis method is disclosed in literatures (Nazeeruddin M K, et al. "Acid-base equilibria of (2,2'-bipyridyl-4,4'-dicarboxylic acid)ruthenium(II) complexes and the effect of protonation on charge-transfer sensitization of nanocrystalline titania", Inorganic Chemistry, Vol. 38, No. 26, pp 6298-6305, 1999).

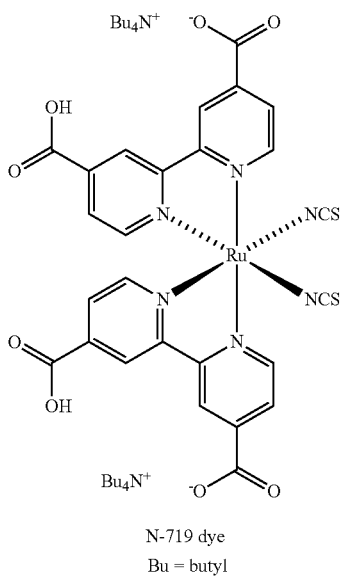

[Formula 88]

N-719 dye

Bu = butyl

Comparative Example

In order to measure the photo-conversion efficiency of a dye-sensitized solar cell according to Examples 1 to 8 and Comparative Test Example in the present invention, photovoltage and photo-current were measured. As a light source, a Xenon lamp (Oriel, 01193) was used, and the solar condition (AM 1.5) of the Xenon lamp was corrected by a standard solar cell (Frunhofer Institute Solare Engeriessysteme, Certificate No. C-ISE369, Type of material: Mono-Si+KG filter). From the measured photo-current/voltage curve, the photo-conversion efficiency was calculated in accordance with Mathematical equation 1 below and noted in Table 1.

$$\eta_e = (Voc \cdot Jsc \cdot FF)/(Pinc) \quad \text{[Mathematical equation 1]}$$

In Mathematical equation 1, $\eta_e$ represents photo-conversion efficiency (Efficiency), Jsc represents current density, Voc represents voltage, FF represents Fill factor, and Pinc represents 100 mw/cm² (1 sun).

TABLE 1

| Dye | Solvent | Jsc(mA/cm²) | Voc(V) | FF | η(%) |
|---|---|---|---|---|---|
| N719 | Ethanol | 14.89 | 0.7 | 0.58 | 6.13 |
| Formula 6 | Ethanol | 14.16 | 0.7 | 0.62 | 6.19 |
| Formula 8 | Ethanol | 16.58 | 0.72 | 0.59 | 7.05 |
| Formula 16 | Ethanol | 16.66 | 0.72 | 0.61 | 7.24 |
| Formula 48 | Ethanol | 15.11 | 0.69 | 0.6 | 6.25 |
| Formula 55 | Ethanol | 17.48 | 0.64 | 0.66 | 7.4 |
| Formula 61 | Ethanol | 14.25 | 0.77 | 0.66 | 7.02 |
| Formula 64 | Ethanol | 17.62 | 0.71 | 0.6 | 7.57 |
| Formula 74 | Ethanol | 15.93 | 0.7 | 0.57 | 6.28 |

Figure 2:
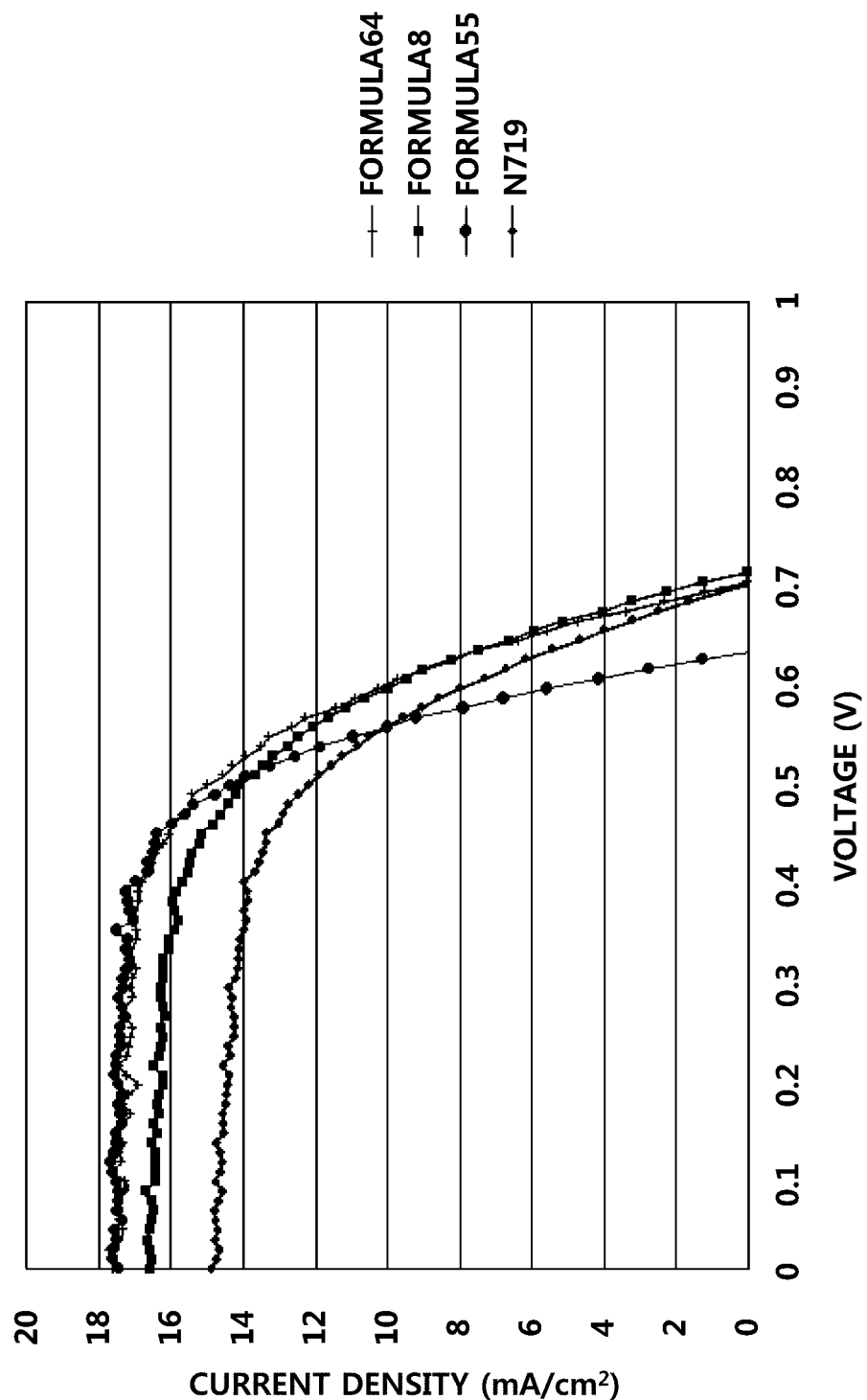
FIG. 2 shows photoconversion efficiency according to an embodiment of the present invention.

FIG. 2 shows photoconversion efficiency according to an embodiment of the present invention. Referring to FIG. 2, the photoconversion efficiency of the dye-sensitized solar cell employing the organic metal dye represented by Formulas 8, 55, and 64 can be compared with the photoconversion efficiency of the dye-sensitized solar cell employing N719 (Formula 88).

In order to measure the molar extinction coefficient and the band gap of the dye-sensitized solar cell according to Examples 1 to 8 in the present invention, a UV/Vis absorption spectrometer and a Cyclic voltammetry were used.

TABLE 2

| Dye | $Abs_{max}$ [nm] | e $[M^{-1}cm^{-1}]$ | HOMO (eV) | LUMO (eV) | Bandgap (eV) |
|---|---|---|---|---|---|
| N719 | 524 | 12,329 | 5.45 | 3.85 | 1.6 |
| Formula 6 | 546 | 12,813 | 5.07 | 3.35 | 1.72 |
| Formula 8 | 551 | 15,113 | 5.03 | 3.34 | 1.72 |
| Formula 16 | 548 | 18,313 | 4.95 | 3.36 | 1.67 |
| Formula 48 | 536 | 12,892 | 4.95 | 3.28 | 1.67 |
| Formula 55 | 567 | 21,136 | 4.92 | 3.31 | 1.61 |
| Formula 61 | 556 | 15,571 | 5.11 | 3.34 | 1.77 |
| Formula 64 | 576 | 26,613 | 5.22 | 3.61 | 1.61 |
| Formula 74 | 584 | 14,916 | 5.01 | 3.34 | 1.61 |

Figure 3:
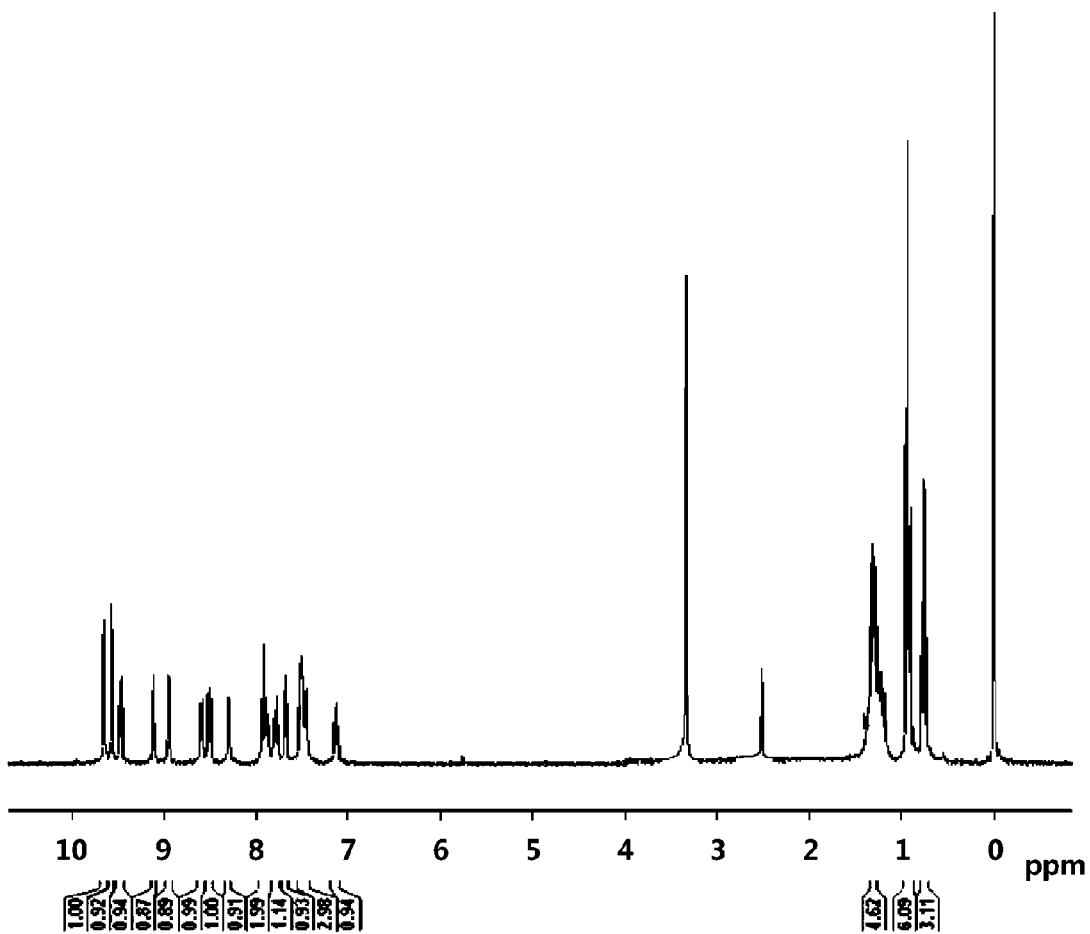
FIG. 3 shows NMR spectrum of Formula 8, according to an embodiment of the present invention.

FIG. 3 shows NMR spectrum of Formula 8, according to an embodiment of the present invention.

As noted in Tables 1, and 2 and FIGS. 2, and 3, it can be seen that as compared to that in an organic metal complex employing a conventional bipyridine derivative as a ligand, in the inventive compound from Examples 1 to 8, the maximum absorption wavelength was shifted to a longer wavelength, the molar extinction coefficient was increased, and the higher photoconversion efficiency was achieved.

As described above, according to the present invention, there is provided a photo sensitized organic metal dye that shows a high molar extinction coefficient and a high photo-conversion efficiency. Also, a dye-sensitized solar cell employing the organic metal dye is excellent in light absorptivity and photoelectric conversion efficiency.

In the above description of Examples and Comparative Examples, the organic metal dye represented by Formulas 1 to 3 was employed in the dye-sensitized solar cell. However, for the person skilled in the art, it should be understood that when the organic metal dye represented by Formulas 1 to 3 is employed in photoelectric elements other than the dye-sensitized solar cell, it is excellent in light absorptivity and photoelectric conversion efficiency.

In addition, since terms, such as "including," "comprising," and "having" mean that one or more corresponding components may exist unless they are specifically described to the contrary, it shall be construed that one or more other components can be included. All of the terminologies containing one or more technical or scientific terminologies have the same meanings that persons skilled in the art understand ordinarily unless they are not defined otherwise. A term ordinarily used like that defined by a dictionary shall be construed that it has a meaning equal to that in the context of a related description, and shall not be construed in an ideal or excessively formal meaning unless it is clearly defined in the present specification.

The above description of the technical spirit of the present invention is illustrative only. Those skilled in the art will appreciate that various modifications, additions and substitutions are possible, without departing from the scope and spirit of the invention. Therefore, the embodiments disclosed in the present invention are intended to illustrate the scope of the technical idea of the present invention, and the scope of the present invention is not limited by the embodiment. The scope of the present invention shall be construed on the basis of the accompanying claims in such a manner that all of the technical ideas included within the scope equivalent to the claims belong to the present invention.

CROSS-REFERENCE TO RELATED APPLICATIONS

This application is a U.S. National Phase Application under 35 U.S.C. §371 of International Application No. PCT/KR2010/008515 filed on Dec. 1, 2010 and published in Korean as WO2011/068346 A2, which is incorporated herein by reference. This application claims priority from and the benefit under 35 U.S.C. §119(a) of Korean Patent Application No. 10-2009-0118654, filed on Dec. 2, 2009, which is hereby incorporated by reference for all purposes as if fully set forth herein. Further, this application claims the benefit of priority in other countries than U.S., which are hereby incorporated by reference herein.

The invention claimed is:

1. An organic metal dye represented by Formula below:

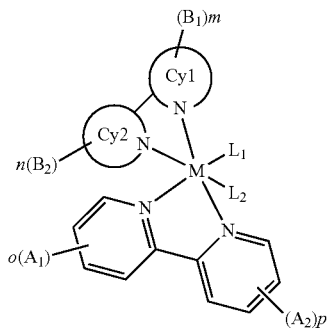

wherein Cy1, and Cy2 each represents a pyridine group or a nitrogen-containing fused heteroaryl group having 5 to 40 carbon atoms, M represents a metal selected from the group consisting of Ru, Os and Fe, $L_1$ and $L_2$ each is independently selected from the group consisting of $H_2O$, —Cl, —I, —CN, —NCO and —NCS, $A_1$, $A_2$, $B_1$ and $B_2$ each is independently selected from the group consisting of substituted or unsubstituted alkyl, substituted or unsubstituted alkenyl, substituted or unsubstituted alkynyl, substituted or unsubstituted aryl and substituted or unsubstituted heteroaryl, and m, n, o and p each is an integer from 1 to 20.

2. The organic metal dye as claimed in claim 1, wherein:
at least one of $A_1$, $A_2$, $B_1$ and $B_2$ comprises at least one anchoring group selected from the group consisting of COOH, $PO_3H_2$, $PO_4H_2$, $SO_4H_2$, CONHOH and deprotonated forms thereof, and
when m to p each is an integer greater than 1, a plurality of $A_1$, $A_2$, $B_1$ and $B_2$ are independently same or different.

3. The organic metal dye as claimed in claim 1,
wherein at least one of $A_1$, $A_2$, $B_1$, or $B_2$, is substituted with a substituent selected from the group consisting of a hydrogen atom, a deuterium atom, a halogen atom, a cyano group, a nitro group, a C1 to C10 alkyl silyl group, a C1 to C40 alkyl group, a C1 to C40 alkoxy group, a C1 to C40 alkyl amino group, a C6 to C40 aryl group, a C6 to C40 aryloxy group, a C6 to C40 arylamino group, a C6 to C40 arylsilyl group, and a C3 to C40 heteroaryl group.

4. The organic metal dye as claimed in claim 3, wherein $A_1$, $A_2$, $B_1$, and $B_2$ and the substituent are linked to each other to form a saturated or unsaturated ring.

5. The organic metal dye as claimed in claim 1,
wherein from among $A_1$, $A_2$, $B_1$ and $B_2$, at least one terminal group is one anion selected from the group consisting of $COO^-$, $PO^{2-}_3$, $PO^{2-}_4$, $SO^{2-}_3$, $SO^{2-}_4$, and $CONHO^-$, and the terminal group forms a salt in combination with one cation selected from the group consisting of ammonium, phosphonium, sulfonium, imidazolium, pyrrolidonium and pyridinium.

6. A photoelectric element comprising a porous oxide semiconductor film comprising the organic metal dye as claimed in claim 1.

7. The photoelectric element as claimed in claim 6, wherein the porous oxide semiconductor film comprises fine particles comprising, as a main material, an oxide of titanium, tin, zinc, tungsten, zirconium, gallium, indium, yttrium, niobium, tantalum, or vanadium.

8. The photoelectric element as claimed in claim 7, wherein the porous oxide semiconductor film is used in a light absorbing layer formed between a first electrode and a second electrode, the second electrode being disposed opposingly to the first electrode.

9. The photoelectric element as claimed in claim 8, wherein a thickness of the porous oxide semiconductor film is 1 to 2,000 nm.

10. The photoelectric element as claimed claim 6, which is a solar cell.

11. A dye-sensitized solar cell comprising:
a first electrode;
a light absorbing layer formed on any one surface of the first electrode, the light absorbing layer comprising a porous film and the organic metal dye formed on the porous film, as claimed in claim 1;
a second electrode that is disposed opposingly to the first electrode having the light absorbing layer formed thereon; and
an electrolyte filled up in a space between the first electrode and the second electrode.

12. The organic metal dye as claimed in claim 1, wherein Formula above is represented by Formula below:

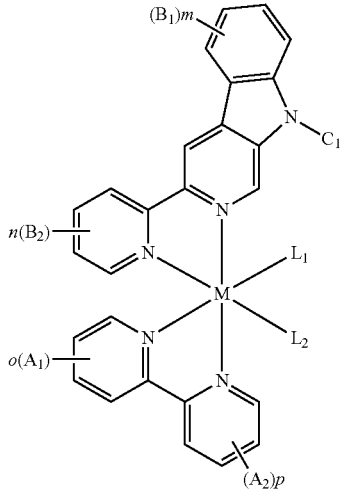

wherein $C_1$ is selected from the group consisting of substituted or unsubstituted alkyl, substituted or unsubstituted alkenyl, substituted or unsubstituted alkynyl, substituted or unsubstituted aryl and substituted or unsubstituted heteroaryl.

13. The organic metal dye as claimed in claim 12, wherein at least one of $A_1$, $A_2$, $B_1$, $B_2$, or $C_1$ is substituted with a substituent selected from the group consisting of a hydrogen atom, a deuterium atom, a halogen atom, a cyano group, a nitro group, a C1 to C10 alkyl silyl group, a C1 to C40 alkyl group, a C1 to C40 alkoxy group, a C1 to C40 alkyl amino group, a C6 to C40 aryl group, a C6 to C40 aryloxy group, a C6 to C40 arylamino group, a C6 to C40 arylsilyl group, and a C3 to C40 heteroaryl group.

14. The organic metal dye as claimed in claim 1, wherein Formula above is represented by Formula below:

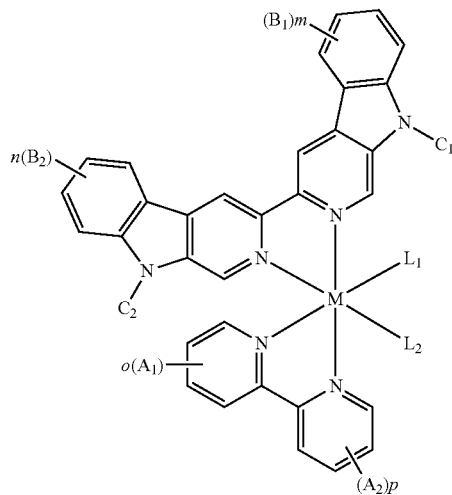

wherein $C_1$ and $C_2$ each is independently selected from the group consisting of a hydrogen atom, a deuterium atom, a halogen atom, a cyano group, a nitro group, substituted or unsubstituted alkyl, substituted or unsubstituted alkenyl, substituted or unsubstituted alkynyl, substituted or unsubstituted aryl and substituted or unsubstituted heteroaryl.

15. The organic metal dye as claimed in claim 14, wherein at least one of $A_1$, $A_2$, $B_1$, $B_2$, $C_1$, or $C_2$ is substituted with a substituent selected from the group consisting of a hydrogen atom, a deuterium atom, a halogen atom, a cyano group, a nitro group, a C1 to C10 alkyl silyl group, a C1 to C40 alkyl group, a C1 to C40 alkoxy group, a C1 to C40 alkyl amino group, a C6 to C40 aryl group, a C6 to C40 aryloxy group, a C6 to C40 arylamino group, a C6 to C40 arylsilyl group, and a C3 to C40 heteroaryl group.

* * * * *